(12) United States Patent
Kwok et al.

(10) Patent No.: US 11,674,877 B2
(45) Date of Patent: Jun. 13, 2023

(54) APPARATUS AND METHOD FOR CYCLIC FLOW CYTOMETRY USING PARTICULARIZED CELL IDENTIFICATION

(71) Applicant: LASE Innovation Inc., Cambridge, MA (US)

(72) Inventors: Sheldon J. J. Kwok, Boston, MA (US); Han Zhu, Cambridge, MA (US)

(73) Assignee: LASE Innovation Inc., Woburn, MA (US)

(*) Notice: Subject to any disclaimer, the term of this patent is extended or adjusted under 35 U.S.C. 154(b) by 264 days.

(21) Appl. No.: 17/166,524

(22) Filed: Feb. 3, 2021

(65) Prior Publication Data
US 2021/0239590 A1    Aug. 5, 2021

Related U.S. Application Data

(60) Provisional application No. 62/969,380, filed on Feb. 3, 2020.

(51) Int. Cl.
*G01N 15/14*    (2006.01)

(52) U.S. Cl.
CPC ..... *G01N 15/1404* (2013.01); *G01N 15/1425* (2013.01); *G01N 15/1463* (2013.01);
(Continued)

(58) Field of Classification Search
CPC .......... G01N 15/1404; G01N 15/1425; G01N 15/1463; G01N 2015/1402;
(Continued)

(56) References Cited

U.S. PATENT DOCUMENTS

| 9,934,364 B1* | 4/2018 | Kumar | G06N 3/045 |
| 2012/0069170 A1* | 3/2012 | Gesley | G06T 7/0012 |
| | | | 348/79 |
| 2018/0038784 A1* | 2/2018 | Marks | G01N 15/1434 |

FOREIGN PATENT DOCUMENTS

| WO | 2017/210675 A1 | 12/2017 |
| WO | 2019/040599 A1 | 2/2019 |

OTHER PUBLICATIONS

Krutzik Po et al: "Fluorescent cell barcoding in flow cytometry allows high-throughput drug screening and signaling profiling", Nature Methods, Nature Pub. Group, New York, vol. 3. No. 5, Jan. 1, 2006, pp. 361-368, XP009088833, ISSN: (Year: 2006).*

(Continued)

*Primary Examiner* — Roy M Punnoose
(74) *Attorney, Agent, or Firm* — Sunstein LLP

(57) ABSTRACT

Method of and apparatus for performing cyclic flow cytometry analysis on a sample population of cellular entities including: causing each cellular entity to be labeled with an optical identifier; for each cellular entity, performing a first pass of flow cytometry measurement over a flow channel with respect to a first set of parameters, under conditions of determining an identification for the cellular entity for which values of the first set of parameters are being obtained, and storing the values of the first set in association with the identification; and performing a second pass of flow cytometry measurement over the flow channel with respect to a second set of parameters, under conditions of separately determining an identification for the cellular entity for which values of the second set of parameters are being obtained, and storing the values of the second set in association with the identification.

24 Claims, 26 Drawing Sheets

(52) U.S. Cl.
CPC ............... *G01N 2015/1402* (2013.01); *G01N 2015/1497* (2013.01)

(58) Field of Classification Search
CPC ....... G01N 2015/1497; G01N 15/1429; G01N 2015/1006; G01N 2015/1438; G01N 2015/1477; G01N 2015/149; G01N 2015/1493; G01N 15/1459; G01N 33/569
See application file for complete search history.

(56) References Cited

OTHER PUBLICATIONS

Krutzik et al—"Flourescent cell barcoding in flow cytometry allows high-throughput drug screening and signaling profiling", Nature Methods, vol. 3, No. 5, May 2006, pp. 361-368.
International Searching Authority—International Search Report—International Application No. PCT/US2021/016370, dated May 26, 2021, together with the Written Opinion of the International Searching Authority, 15 pages.

* cited by examiner

APPARATUS AND METHOD FOR CYCLIC FLOW CYTOMETRY USING PARTICULARIZED CELL IDENTIFICATION

CROSS-REFERENCE TO RELATED APPLICATIONS

The present application claims priority to U.S. Provisional Application No. 62/969,380 entitled "Apparatus and Method for Cyclic Flow Cytometry Using Particularized Cell Identification" and filed on Feb. 3, 2020. The foregoing application is hereby incorporated by reference in its entirety.

TECHNICAL FIELD

The present invention relates to apparatus and methods for flow cytometry, and more particularly to apparatus and methods allowing repeated measurements of a population of cellular entities using particularized cell identification.

BACKGROUND ART

Flow cytometry is an analysis technique to measure the physical and chemical characteristics of single cells in a rapidly flowing stream. Modern flow cytometry uses fluorescent probes to detect specific molecules or molecular complexes, such as surface membrane proteins, intracellular signaling proteins, and RNA molecules. Flow cytometry enables identification and quantification of different cell types within a population of cells, determination of phenotypes and gene expression patterns, and detection of biomarkers associated with diseases. Such information is obtained at single-cell resolution and is widely used for diagnostics, treatment monitoring, drug discovery as well as basic biological investigations.

A typical workflow involves first staining of a suspension of cells (typically $10^5$ to $10^6$ cells) with a mixture of fluorophore-conjugated antibodies that bind to different cellular markers. Next, the cells are injected in the flow cytometer instrument where cells are flowed one at a time past a laser beam that excites the fluorophores present on each cell. State-of-the-art flow cytometers are able to make measurements of cells at rates of 10,000 cells per second or more. The fluorescence emission from each cell is collected and analyzed to reveal the presence or absence of the different markers. For research and drug development, flow cytometry is commonly used to analyze cells treated with different drugs or environmental conditions to assess effects on viability, apoptosis, cell cycle, and proliferation. Blood samples are commonly analyzed with flow cytometers to characterize different cell types, a technique called immunophenotyping, which is widely employed in immunology and immuno-oncology research, disease diagnosis, and treatment monitoring. Besides cells, emerging applications of flow cytometry include analysis of multicellular spheroids, bacterial cells, and cellular components such as nuclei and vesicles.

The ability to detect multiple markers per cell is the key to the vast majority of applications of flow cytometry. In general, detecting more markers enables more detailed and accurate analysis of cells. Over the past few decades, flow cytometry users are measuring increasingly more markers per cell. For example, in 2001, a report found that no clinical applications required 5 or more markers per cell (International Clinical Cytometry Society). By 2015, the majority of clinical users measure 10 markers or more, particularly for hematological applications such as diagnosis and monitoring of leukemia and lymphoma. (2015 Global Survey on Flow Cytometry Trends).

Recent development of sophisticated flow cytometers and increased availability of different fluorophores and high-affinity antibodies have enabled high-parameter flow cytometry with more than 15 markers. High-parameter flow cytometry has accelerated the development of immunotherapy, a new branch of medicine that seeks to exploit the patient's own immune system for curing illnesses. As immunotherapy emerges as a viable approach to treat cancers and genetic abnormalities, comprehensive subcategorization and characterization of immune cells have become crucial, rendering high-parameter flow cytometry an essential technology for both academic and clinical research.

However, one of the major limitations of current flow cytometry is the limited number of fluorescence probes that can be used simultaneously. This is because spectral overlap of their photoluminescence. The fluorescence emission of a fluorescence probe occupies a spectral range of about 30-100 nm in wavelength. Therefore, over a wavelength range from 400 to 800 nm, typically no more than 10 different fluorescence probes can be easily distinguished. The number of multiplexable probes can be increased by utilizing multiple excitation lasers with different excitation wavelengths to measure difference in absorption spectra between probes. To be able to discriminate fluorophores with spectral overlap, a mathematical process called spectral compensation is performed, which also involves optimizing the acquisition settings of the instrument to best distinguish the different fluorophores. When spectral overlap is severe as is the case when more than 10 fluorophores are used simultaneously, spectral compensation significantly degrades data quality and hinders accurate biological interpretation. As a result, the number of simultaneously-usable probes is limited to about 30 to 40 even for the most sophisticated, state-of-the-art instruments.

Proper selection of a set of the fluorescent staining reagents (often called a panel) is a major challenge and time-consuming procedure when measuring multiple markers at once. First, different fluorophores with minimal spectral overlap should be chosen to enable unambiguous detection of the different markers. Second, fluorophore brightness should be matched to the expected abundance of the protein marker in the cell (brighter fluorophores for less abundant proteins). Finally, steric hindrance between antibodies should be considered when attempting to label many markers at once. Following the initial panel design, the panel performance should be validated with a flow cytometer by analyzing control samples stained separately with each fluorophore-antibody conjugate from the panel. This process includes spectral compensation, in which the settings of the instrument are optimized to best distinguish the different fluorophores in the panel. Often, failed performance validation results in partial or complete re-design of the panel itself.

In all, the iterative panel design and validation process can take weeks to months to complete depending on the number of markers required. For applications requiring 8 markers or fewer, this process is streamlined (<1 week) owing to the availability of easily distinguishable combinations of fluorophores. Preparation of panels of 15 or more marker panels is arduous, requiring over a month of optimization by an experienced flow cytometry user. In addition, for these high marker panels, limited availability of antibodies with suitable fluorophores can be a major barrier, often requiring custom orders with long lead times and requiring further validation.

Reagent costs are also significant and potentially cost prohibitive for large panel flow cytometry. A number of control samples are necessary to optimize flow cytometry acquisition settings including single-stained controls to optimize spectral compensation and fluorescence minus-one (FMO) controls to optimize gating and classification of fluorescent signals for each marker. For FMO controls, cells are stained with every antibody in the panel but one as a negative control for the antibody/marker that is not included. Therefore, for a 15-marker panel, there would be at least 15 FMO control samples each requiring 14 antibodies to target 14 of the 15 markers.

As mentioned, spectral overlap becomes overwhelming when more than 30 markers are to be measured at once, and it is very challenging for conventional flow cytometry to measure 30-40 markers.

When measurement of more than 30-40 markers are needed, other types of molecular analysis tools such as single-cell mass spectrometry and single-cell sequencing are used instead of flow cytometry. While these other tools can meet this need, they are typically more expensive and have much lower throughput rates. An innovation that solves the multiplexing problems of fluorescence-based flow cytometry at low cost and high throughput will have a high impact for single-cell analysis.

SUMMARY OF THE EMBODIMENTS

In accordance with an embodiment of the invention, there is provided a method of performing cyclic flow cytometry analysis on a sample population of cellular entities. The method of this embodiment includes causing each cellular entity in the population to be labeled with an optical identifier. The method further includes, for each cellular entity in the population, performing a first pass of flow cytometry measurement over a flow channel with respect to a first set of parameters under conditions of determining an identification for the cellular entity for which attributes of the first set of parameters are being obtained, and storing the attributes of the first set in association with the identification. The method further includes, for each cellular entity in the population, performing a second pass of flow cytometry measurement over the flow channel with respect to a second set of parameters, under conditions of separately determining an identification for the cellular entity for which attributes of the second set of parameters are being obtained, and storing the attributes of the second set in association with the identification.

A further related embodiment of the invention includes, for each cellular entity in the population, using the identification to combine attributes of the first set of parameters with attributes of the second set of parameters. In another related embodiment, the method also includes performing at least one additional pass of flow cytometry measurement over the flow channel with respect to a at least one additional set of parameters, under conditions of separately determining an identification for the cellular entity for which values of the at least one additional set of parameters are being obtained, and storing the values of the at least one additional set in association with the identification.

Alternatively or in addition, the first and second passes of flow cytometry measurement use first and second sets of fluorescent probes respectively targeting distinct sets of parameters, and the method further includes, after performing the first pass of flow cytometry measurement and before performing the second pass of flow cytometry measurement, inactivating the first set of fluorescent probes.

Also alternatively or in addition, the sample population includes at least 1,000 cellular entities. In another related embodiment, the method also includes, after performing the first pass of flow cytometry measurement and before performing the second pass of flow cytometry measurement, collecting the population that has been made the subject of the analysis in a manner preserving characteristics of the cellular entities of the population.

Alternatively or in addition, collecting includes using a collection vessel at an end of the flow channel to capture the cellular entities of the population. Also alternatively or in addition, the method includes reconditioning the captured cellular entities before performing the second pass of flow cytometry measurement.

In a related embodiment of the invention, the optical identifier is a set of micro-laser particles. Alternatively or in addition, the micro-laser particles include a semiconductor.

In a further related embodiment of the invention, the flow cytometry measurements utilize fluorescence by fluorophores, and determining the identification for the cellular entity includes reading the optical identifier in an emission frequency spectrum using a light excitation source. Alternatively or in addition, the fluorophores are configured to operate in a fluorescence frequency spectrum separate from the emission frequency spectrum. Also alternatively or in addition, the fluorophores are configured to be photobleachable within 30 minutes without affecting cell viability.

In a related embodiment, the first set of parameters is selected from the group consisting of surface or intracellular protein expression, RNA expression, quantification of organelles (such as mitochondria and lysosomes), cell granularity, cell size, cell shape and combinations thereof. Alternatively or in addition, each such parameter of the cellular entity is measured by a phenomenon selected from the group consisting of fluorescence, light scattering, and absorption.

In accordance with an alternative embodiment of the invention, an improved flow cytometry apparatus is of the type having a flow channel coupled to a flow input configured to receive a sample population of cellular entities to be measured, with respect to a target set of parameters. The flow channel is being instrumented for obtaining and storing successive fluorescence readings from successive cellular entities passing therethrough. The improvement includes an OFID reader associated with the flow channel, wherein each cellular entity in the sample population has been tagged with an optical identifier, and the OFID reader is configured to determine an identification of each cellular entity as it is being measured in each pass of a plurality of passes of the sample population of cellular entities through the flow channel, each pass associated with a corresponding target set of parameters.

Alternatively or in addition, the OFID reader is configured to operate over a plurality of emission collection paths, of which two thereof define an angle of approximately 90 degrees with respect to each other.

In a related embodiment, the improvement further includes a recirculator configured to recondition cellular entities that have passed through the flow channel and to position them for a further pass through the flow channel.

In accordance with yet another embodiment of the invention, an improved flow cytometry apparatus is of the type having a flow channel coupled to a flow input configured to receive a sample population of cellular entities to be measured, with respect to a target set of parameters. The flow channel is being instrumented for obtaining and storing successive fluorescence readings from successive cellular entities passing therethrough. The improvement includes an OFID reader associated with the flow channel, wherein each cellular entity in the sample population has been tagged with an optical identifier and the OFID reader is configured to determine an identification of each cellular identity as it is being measured in each pass of a plurality of passes of the sample population of cellular entities through the flow channel, each pass associated with a corresponding target set of parameters. The improvement further includes a processor (i) to associate and store in a storage device a corresponding fluorescence reading with the identification of each cellular entity in each of the passes and (ii) to use the identification to combine attributes of the corresponding target sets of parameters.

Alternatively or in addition, the OFID reader is configured to operate over a plurality of emission collection paths of which two thereof define an angle of approximately 90 degrees with respect to each other.

Also alternatively or in addition, the improved flow cytometry apparatus includes a recirculator configured to capture and recondition cellular entities that have passed through the flow channel and to position them for a further pass through the flow channel. Also alternatively or in addition, the recirculator has a surface, for contacting the population of cellular entities, that is configured to have low wettability.

In accordance with yet another embodiment of the invention, an improved flow cytometry apparatus is of the type having a flow channel coupled to a flow input configured to receive a sample population of cellular entities to be measured, with respect to a target set of parameters. The flow channel is being instrumented for obtaining and storing successive fluorescence readings from successive cellular entities passing therethrough. The improvement includes an OFID reader associated with the flow channel, wherein each cellular entity in the sample population has been tagged with an optical identifier and the OFID reader is configured to determine an identification of each cellular identity as it is being measured as the cellular entity pass through the flow channel, wherein the OFID reader is configured to operate over a plurality of emission collection paths of which two thereof define an angle of approximately 90 degrees with respect to each other. The improvement further includes a processor (i) to associate and store in a storage device a corresponding fluorescence reading with the identification of each cellular entity in each of the passes and (ii) to use the identification to combine attributes of the corresponding target set of parameters.

In accordance with yet another embodiment of the invention, a kit is provided for converting a flow cytometry apparatus, of the type having a flow channel coupled to a flow input configured to receive a sample population of cellular entities to be measured, with respect to a target set of parameters, the flow channel being instrumented for obtaining and storing successive fluorescence readings from successive cellular entities passing therethrough, into an improved flow cytometry apparatus. The kit includes an OFID reader associated with the flow channel, wherein each cellular entity in the sample population has been tagged with an optical identifier and the OFID reader is configured to determine an identification of each cellular entity as it is being measured in each pass of a plurality of passes of the sample population of cellular entities through the flow channel, each pass associated with a corresponding target set of parameters. The kit further includes a recirculator configured to capture and recondition cellular entities that have passed through the flow channel and to position them for a further pass through the flow channel. The kit also includes a processor (i) to associate and store in a storage device a corresponding fluorescence reading with the identification of each cellular entity in each of the passes and (ii) to use the identification to combine attributes of the corresponding target sets of parameters.

BRIEF DESCRIPTION OF THE DRAWINGS

The foregoing features of embodiments will be more readily understood by reference to the following detailed description, taken with reference to the accompanying drawings, in which:

FIG. 2A shows microparticle delivery into a cell through endocytosis in accordance with an embodiment of the present invention. FIG. 2B show microparticle delivery into a cell through liposome carriers in accordance with another embodiment of the present invention. FIG. 2C shows microparticle delivery into a cell through biolistic particle bombardment in accordance with a further embodiment of the present invention. FIG. 2D shows microparticle conjugation to the cell surface in accordance with another embodiment of the present invention. FIG. 2E shows an optical image of a micro-laser particle (LPs) tagged to the cell surface (left) and inside the cell (right) in accordance with embodiments of the present invention.

FIG. 4A shows processes in conventional flow cytometry. FIG. 4B shows processes in an initial run of a cyclic flow cytometry analysis in accordance with an embodiment of the present invention FIG. 4C shows processes in cyclic flow cytometry, using optical identifiers as well as de-staining and staining with fluorescence probes, in accordance with an embodiment of the present invention. FIG. 4D shows processes in cyclic flow cytometry, using optical identifiers and sequential fluorescence reading with DNA-barcoded probes, in accordance with another embodiment of the present invention.

FIG. 6A shows an electron microscope image of a silica-coated semiconductor microlaser particle and its typical stimulated-emission spectrum with a peak at 1392 nm and a full-width-at-half-maxima of 0.35 nm. FIG. 6B shows a fluorescence microscope image of a cell comprising three micro-laser particles with different laser emission peaks. FIG. 6C shows an optical image of an optical identifier comprising three microdisk lasers. FIG. 6D illustrates the emission spectrum from the triplet laser particles. The three narrow spectral peaks define the unique OFID conferred by the optical identifier.

FIG. 7A shows a system using multiple optical fibers to collect light from micro-laser particles. FIG. 7B depicts an alternative optical configuration using two collection paths and free-space optics only. FIG. 7C depicts an alternative optical configuration using three collection paths with respect to a typical flow cell. FIG. 7D depicts a 3-dimensional illustration of the optical configuration in FIG. 7C.

FIG. 9A shows data obtained with two samples consisting of Human Jurkat T cells without micro-laser particles (left) and tagged with micro-laser particles (right), respectively. FIG. 9B shows data obtained with two samples consisting of human peripheral blood mononuclear cells (PBMCs) without micro-laser particles (top) and tagged with micro-laser particles (bottom), respectively.

FIG. 10A shows the cumulative percentage of detected spectra for a given collection efficiency in a simulation of randomly oriented microdisk laser particles 1000. FIG. 10B shows exemplary data obtained using a modified flow cytometer prototype, in accordance with embodiments of the present invention.

FIG. 11A shows an exemplary cell associated with micro-laser particle generating an OFID consisting of three spectral peaks that is measured and identified over 8 successive flow cycles of measurement 1100-1114. FIG. 11B shows proof-of-concept flow cytometry data in which THP1 cells tagged with micro-laser particles were analyzed over three flow cycles 1120-1124.

DETAILED DESCRIPTION OF SPECIFIC EMBODIMENTS

Figure 1:
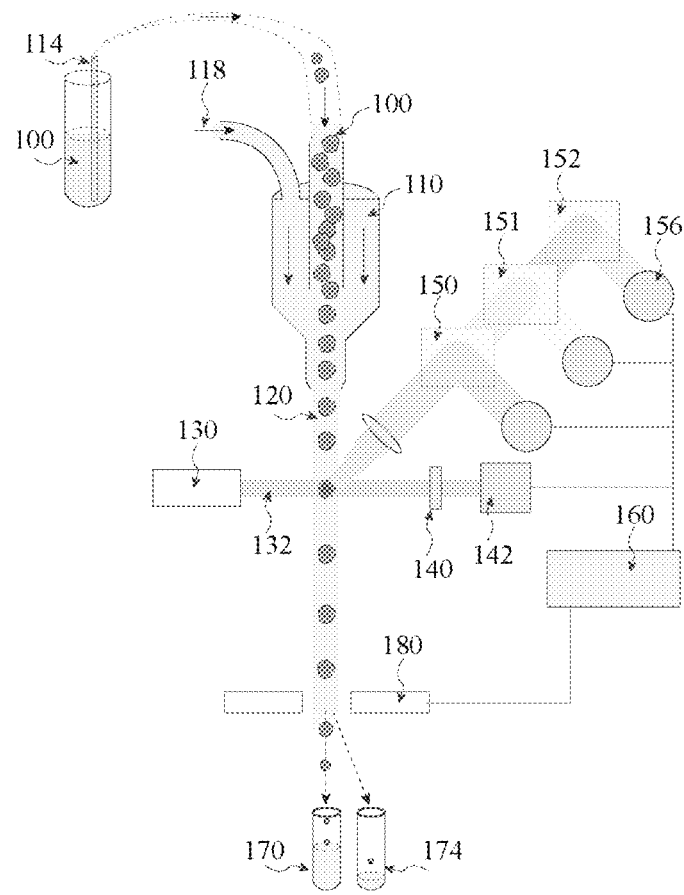
FIG. 1 depicts a conventional flow cytometry instrument.

Definitions. As used in this description and the accompanying claims, the following terms shall have the meanings indicated, unless the context otherwise requires:

A "set" has at least one member.

An "optical identifier" is a set of identifying microparticles, capable of being read optically and being physically associated with a cellular entity that defines a unique identity for the cellular entity. For example, the set of identifying microparticles may be a collection of three micro-laser particles, wherein each microparticle emits a unique frequency of coherent light, when inquired by a suitable excitation, preferably a laser light, based on the particular geometry and composition thereof, and the microparticles have a size smaller than 100 microns. A particle having a size of 10 nm is still a "microparticle" in this context, because it has a size smaller than 100 microns.

A "cellular entity" includes a cell, or a part of a cell, such as a nucleus or vesicle or organelle, or a coherent organization of cells, such as multicellular spheroid. The cellular entity may also be live or chemically fixed.

To "tag" a cellular entity means to cause an optical identifier to be physically associated with the cellular entity.

A "parameter" is a property of a cellular entity measured by flow cytometry, such as surface or intracellular protein expression, RNA expression, quantification of organelles (such as mitochondria and lysosomes), cell granularity, or cell size, or cell shape. Each such parameter of the cellular entity is measured by fluorescence, light scattering, or absorption. Each parameter measurement has a value that is determined by calculation using raw data obtained from the flow cytometry system.

An "OFID reader" is a combination of (i) a light excitation source, such as a laser, to excite an optical identifier to produce a corresponding signal with (ii) a spectrometer to read the corresponding signal to determine an identification based on the optical identifier. The result is optical-frequency identification (OFID).

To "inactivate" a set of fluorescent probes means a process that removes or alters fluorescence associated with the set of probes, or a process that alters the ability of the probes to interact with a specified target, or a process that physically removes the probe from the sample.

A "recirculator" is an apparatus that collects cellular entities after measurement in the flow channel, re-conditions the cells and positions them for a further measurement in the flow channel.

To "recondition" a population of cellular entities that has undergone a first pass flow cytometry measurement cycle targeting a set of parameters means to process the population so that it can be subjected to a next pass flow cytometry measurement cycle to target a further set of parameters. Often, to recondition a population will involve inactivation of probes used in the first pass and re-staining the population.

A "collection path" is defined as a series of optical elements for directing light that is emitted within a solid angle into a detector or spectrometer. The optical elements may include free-space components such as lens and mirrors or fiber optic components. Light from different collection paths are typically directed onto distinct spatial regions of the detector or spectrometer, or combined via a 50/50 beam-splitter or beam-combiner before reaching the detector or spectrometer.

Manufacture and characteristics of identifying microparticles are described in published PCT Application WO2017/210675, which is hereby incorporated herein by reference in its entirety. The present application describes a new use and context for identifying microparticles in a type of flow cytometry that we call "cyclic flow cytometry."

FIG. 1 depicts a conventional flow cytometry instrument. Cells in a sample 100 are stained with fluorescent probes. Typically used probes include fluorescent dyes, fluorescent dyes, fluorophores or fluorochromes conjugated to antibodies or nucleic acids, and genetically encoded fluorescent protein reporters. A flow cell 110 receives the cells 100, through a cannula, tube or motorized pipette 114. The flow cell is also connected to a tube to receive sheath fluid 118. The flow cell generates single-cell droplets or a stream of cells in a flow channel 120. In most cases, the flow channel is vertical and use gravitational fall, but microfluidic channels are also used for more precise control of the flow speed and pressure. The apparatus employs an optical arrangement to measure the optical parameters from individual cells. It comprises one or a few laser sources 130, which deliver excitation light to the cells flowing in file. The forward or side scattering light 132 from each cell is measured by using a laser-line rejection filter 140 and a photodetector, such as single-photon counter, avalanche photodiode (APD) or photomultiplier tubes (PMT) 142. Fluorescence emission is collected through dichroic mirrors 140, 152, and 152, directing different spectral components to different photodetectors or PMT's 150. Instead of the dichroic mirrors and PMT's, a prism and a PMT array (1×4 to 1×16) may be used. The electrical signals from the photodetectors 142 and 156 are connected to a computer 160. The computer determines the magnitude of each fluorescent probe from the electrical signals. When spectra from co-stained fluorescent probes have substantial overlap among themselves, spectral unmixing based on linear or nonlinear fitting, or machine learning is applied.

Cells after the fluorescence measurement are collected in a bin 170. The apparatus may also include a sorting arrangement, typically comprising a deflector 180, which is switched to steer specific cells of interest to a separate bin 174. Typically, the deflector includes one or a pair of electrodes to which a high voltage is applied when the cell of interest passes. This technique is called fluorescence-activated cell sorting (FACS).

Figure 2A:
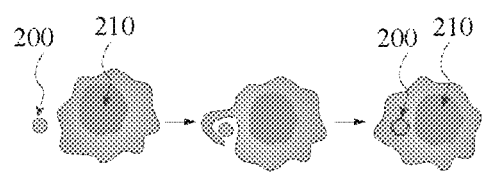
FIGS. 2A through 2E depict different strategies for tagging cells with microparticles in accordance with embodiments of the present invention.
Figure 2B:
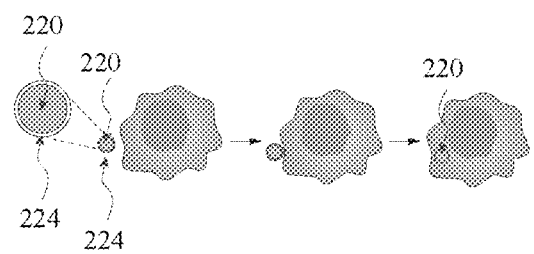

FIGS. 2A through 2E depict different strategies for tagging cells with microparticles in accordance with embodiments of the present invention. FIG. 2A shows microparticle 200 delivery into a cell 210 through endocytosis or macropinocytosis in accordance with an embodiment of the present invention. FIG. 2B show the delivery of a microparticle 220 into a cell through carrier-mediated mechanism, such as by using liposome carriers 224 in accordance with an embodiment of the present invention.

Figure 2C:
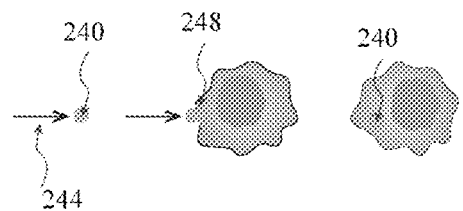

Another strategy involves delivery inside cells by physical means through the cell membrane, including ballistic particle bombardment delivery ("biolistics") or electroporation to generate transient membrane pores. FIG. 2C shows delivery of a microparticle 240 into a cell through biolistic particle bombardment in accordance with a further embodiment of the present invention. The microparticle 240 is sent with a velocity 244 adequate for the microparticle 240 to break through the cell membrane 248.

A further strategy involves biochemical conjugation of microparticles to the cell surface, in which microparticles are tethered to the cell membrane through antibody or chemical binding.

Figure 2D:
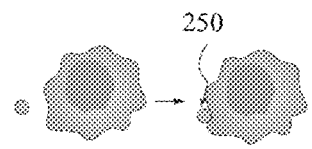
Figure 2E:
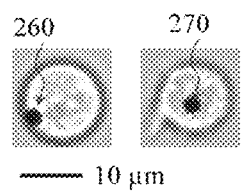

FIG. 2D shows a method to attach a microparticle 250 to the cell surface in accordance with another embodiment of the present invention. FIG. 2E shows two exemplary methods of tagging a microparticle to a cell. It shows an optical image of a semiconductor micro-laser particle 260 tagged to the exterior surface of a cell and another semiconductor micro-laser particle 270 tagged inside a cell (right) in accordance with embodiments of the present invention.

The optimal approach for tagging cells with microparticles depends on the cell type and the type of microparticle used.

Figure 3:
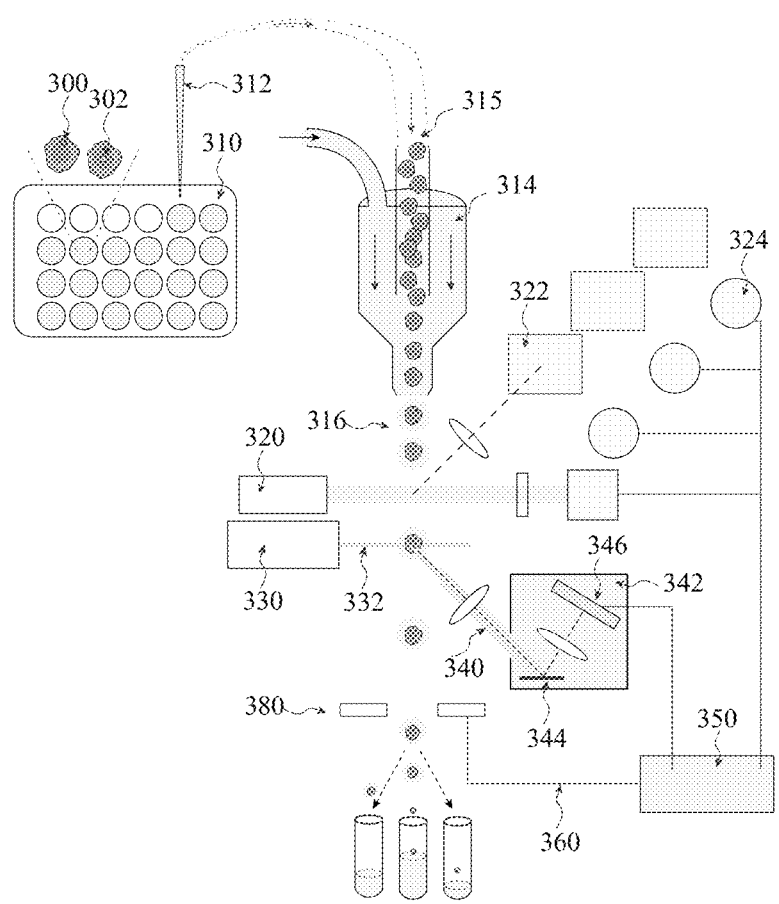
FIG. 3 depicts a modified flow cytometry instrument, combining the conventional fluorescence measurement and a spectrometer to read the optical identifiers, in accordance with an embodiment of the present invention.

FIG. 3 depicts a modified flow cytometry instrument, combining the conventional fluorescence measurement and a spectrometer to read the optical identifiers, in accordance with an embodiment of the present invention. Identifying microparticles 300 and 302 are incorporated into cells. As in the conventional flow cytometry, the cells in a sample 310 is loaded into a flow cell 314 through a flow input 315 using a pipette 312, and the fluorescence emission and light scattering from the cells is measured while the cells are flowing in a flow channel 316. The cells pass through a measurement setup employing an excitation laser source 318, dichroic filter mirror 322, and a PMT 324. The flow cell and accompanying fluidics system are optimized for maximum cell collection after optical measurement.

To read the optical identifiers 300 and 302, the system further employs a pump laser 330, which provides activation or pump light 332 to the cells. A preferred embodiment comprises a pulsed laser 330 producing nanosecond pulses with a repetition rate greater than 1 MHz, but continuous wave laser could be used depending on the identifying microparticles. For micro-laser particles, the peak optical power of the pump beam 332 should be sufficient to reach the threshold lasing intensity.

The emission 340 from the optical identifiers associated with each cell is received and measured in a spectrometer 342. To achieve high spectral resolution better than 1 nm, the spectrometer typically includes at least one diffraction grating 344 and a charge-coupled-device (CCD) camera 346. The output of the camera is connected to a computer 350. The computer 350 is used to identify the optical emission spectra of the microparticles and thereby determine the optical-frequency identification (OFID) of the cells.

The excitation and emission wavelengths of the optical identifiers may be spectrally distinct from the excitation and emission wavelengths of the fluorescent probes. For example, a 1064 nm laser is used to excite (or pump) micro-laser particles that may emit in the 1100 to 1600 nm range, while fluorescent probes are typically excited by visible lasers between 350-700 nm and emit in the 400-800 nm range. Furthermore, the emission spectral shape of the mico-laser particles is significantly narrower than fluorescent probes, with typical linewidths<1 nm, compared to linewidths>50 nm for fluorescent probes. The FACS control signal 360 to a deflector 380 may be based on the fluorescence measurement. Alternatively, if desired, the signal 360 can be based on the measured OFID of a cell.

In some cases, the spectral region of the OFID emission may be overlapped with that of the fluorescence emission from stained cells. In this case, a dichroic filter can no longer adequately separate the OFID emission from cell fluorescence. In this situation, the OFID emission and fluorescence are measured sequentially at different spatial locations (such as upstream and downstream of a flow channel), and the timestamps of each measurement is recorded. The OFID and fluorescence of each cell are then synchronized using the measurement timestamps and the speed of the cell, which is separately measured. Cell speed measurements can be done in various ways depending on the specific fluidic system implementation, such as using flow rate sensors or calibration beads.

In both the conventional cytometry and the modified cytometry illustrated in FIGS. 1 and 2, cells are run through the flow channel one time. In principle, the cells collected in the bin 170 or 174 may be reloaded to the flow channel for repeated measurement to increase accuracy of measurement. Nonetheless, such a repeated measurement, without the use of optical identifiers, does not enable improved multiplexing capability for each single cell that is measured in flow cytometry.

Figure 4A:
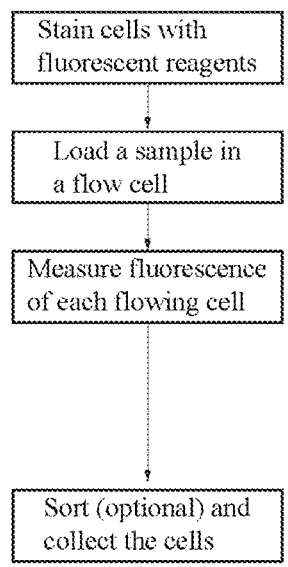
FIGS. 4A through 4D show processes in conventional and cyclic flow cytometry.
Figure 4B:
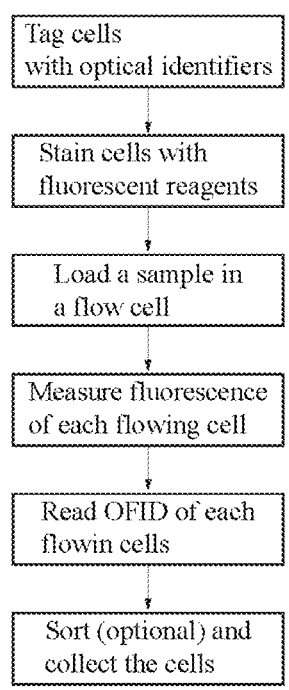
Figure 4C:
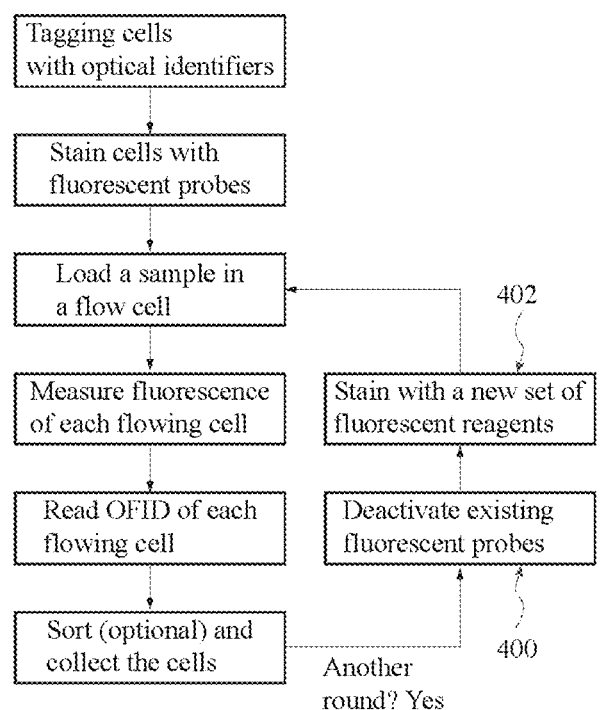
Figure 4D:
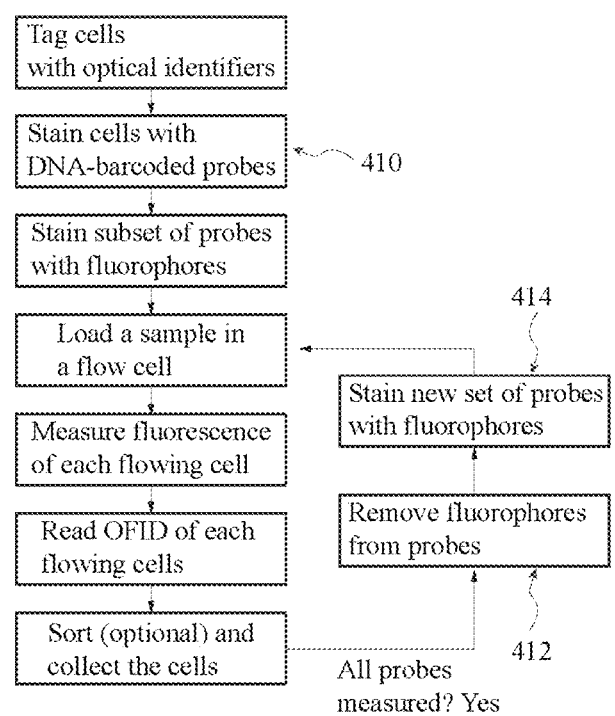

FIGS. 4A through 4D show processes in conventional and cyclic flow cytometry. FIG. 4A shows processes in conventional flow cytometry. FIG. 4B shows processes in an initial pass (run) of a cyclic flow cytometry analysis in accordance with an embodiment of the present invention. FIG. 4C shows processes in cyclic flow cytometry, using optical identifiers as well as de-staining and staining with fluorescence probes, in accordance with an embodiment of the present invention. FIG. 4D shows processes in cyclic flow cytometry, using optical identifiers and sequential fluorescence reading with DNA-barcoded probes, in accordance with another embodiment of the present invention.

In accordance with one embodiment of the invention, the method of cyclic flow cytometry allows cells to be measured multiple times in the same or a different flow channel, and the measurement results from the same cell can be combined together.

In cyclic flow cytometry, cells are collected after each cycle to enable repeated measurements, in accordance with embodiments of the invention. Cells may also be washed between cycles during processing steps such as reconditioning and staining of cells. To maximize collection efficiency of every process, the surface of devices used for cell collection, including components such as tubing, containers, vials and pipettes, may employ suitable materials with low wettability and/or be configured with minimal surface roughness to reduce unwanted cell retention and cell adhesion. Suitable materials include polytetrafluoroethylene, polypropylene, polycarbonate, polyethylene and poly-ether-ether-ketone. Surfaces may also be treated with chemical surfactants to reduce surface tension and prevent cell adhesion, for example using commercially available solutions (Anti-Adherence Rinsing Solution, STEMCell Technologies).

Microfluidic apparatuses may also be used to process and wash cells, including using laminar flow to wash cells with minimal perturbation and maximal retention. Cell collection may also be performed at 4° C. to minimize cell adhesion and maintain cell viability.

A distinctive process in cyclic flow cytometry is the reconditioning of cells after cells are collected following each measurement, in accordance with embodiments of the invention. Cells are inactivated and stained with another set of several, easily distinguishable, fluorescence probes. This process enables measurement of different molecular markers with each cycle.

The reconditioning or de-staining process 400 may involve one of several approaches. One approach involves inactivation or removal of fluorescent probes. This can be achieved through photobleaching of the fluorophores, for example, using white light or blue light from a light source at sufficient optical intensity to inactivate the fluorophores but without impairing cell viability. Another approach involves using chemical compounds to cleave the fluorophores or the probes themselves, for example, using commercially available chemically-releasable antibodies (RE-Alease, Miltenyi Biotec).

After the de-staining process 400, the re-staining process 402 involves labeling the cells with another set of fluorescent probes that are typically different from the previous fluorescent probes.

An alternative to de-staining and re-staining cells with fluorescence probes involves staining the cells with oligonucleotide-barcoded probes that target all the molecular markers of interest at once 410. One example is commercially available DNA-barcoded antibodies (CODEX, Akoya Biosciences). As before, cells are measured in multiple, sequential flow cytometry measurements. At each measurement, fluorophores are added that bind to a subset of the oligonucleotide-barcoded probes 414, and chemicals are added to remove the fluorophores from the previous measurement 412 (other than the first measurement).

Cyclic flow cytometry involves measurement of the properties of each cell multiple times, typically 2 to 4 times or more as needed. 5 cycles or more should also be possible. Cyclic flow cytometry also includes a computational process to assign the fluorescence measurement data obtained over multiple cycles to the same cells based on the measurement of the unique OFIDs of the cells at each cycle.

Figure 5A:
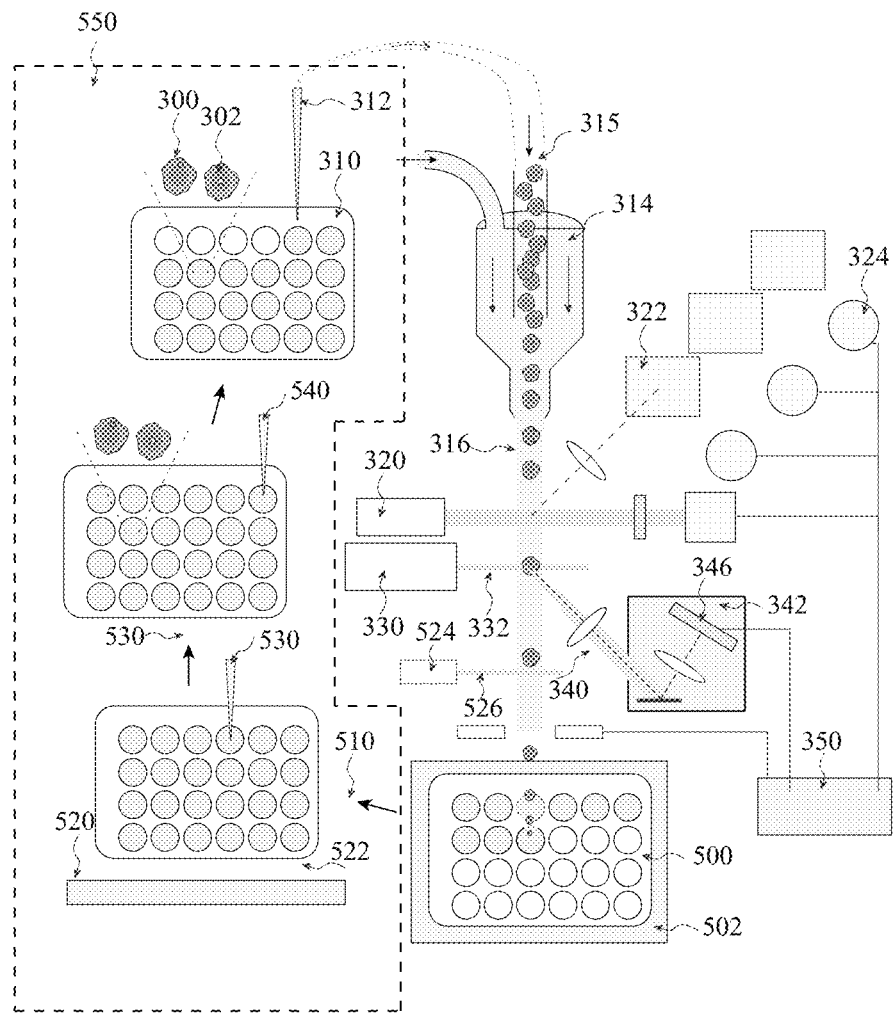
FIGS. 5A-5B depict instruments for cyclic flow cytometry, in accordance with embodiments of the present invention. The instrument for cyclic flow cytometry includes a flow cytometry system for reading fluorescence and optical identifiers as depicted in FIG. 3, and a recirculator apparatus for automating cell processing between cycles of cyclic flow cytometry.
Figure 5B:
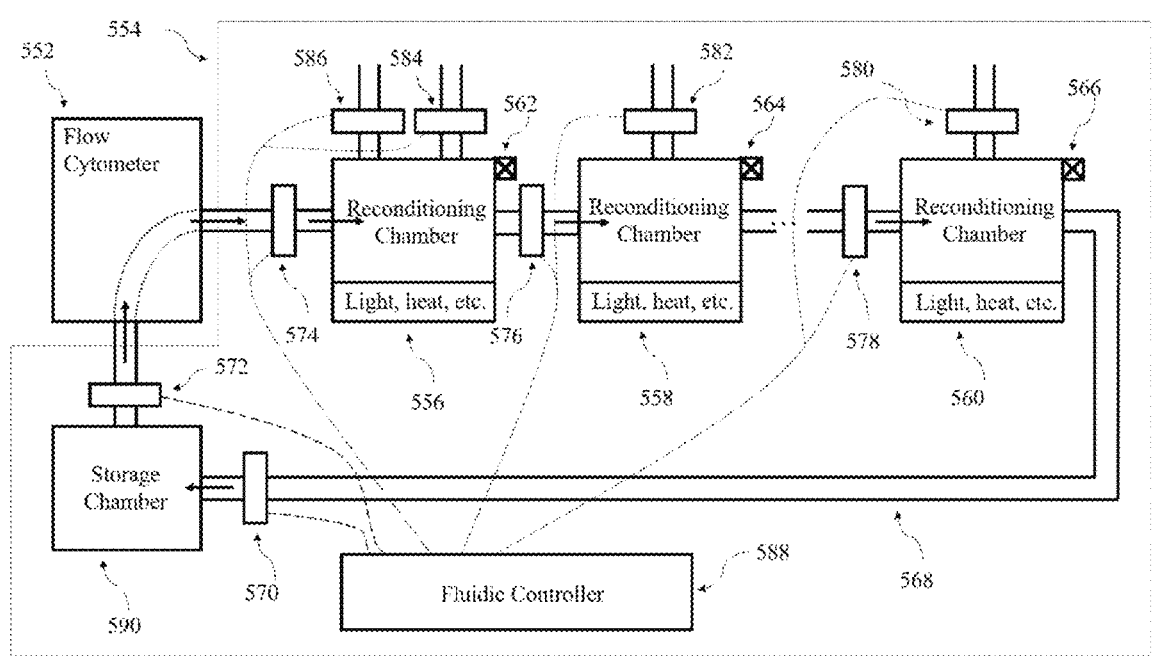

FIGS. 5A through 5B depict instruments for cyclic flow cytometry, in accordance with embodiments of the present invention. The instrument for cyclic flow cytometry includes a flow cytometry system for reading fluorescence and optical identifiers as depicted in FIG. 3, and a recirculator apparatus for automating cell processing between cycles of cyclic flow cytometry.

FIG. 5A shows an instrument for cyclic flow cytometry, which includes the system depicted in FIG. 3 and a recirculator apparatus 550 for cell processing, in accordance with embodiments of the present invention. The recirculator apparatus uses mechanical components including a motorized stage, a sample collection vessel, motorized stage, and motorized pipettes to perform processes including cell collection, cell reconditioning, and cell positioning for each cycle of measurement. Cells from a sample after one cycle of flow measurement are collected into a tube or a well plate 500. The well plate 500 may be mounted on a motorized translational stage 502 to collect cells from different samples in different wells. Then, the collected cells are moved to the re-conditioning process 510. Reconditioning may involve de-staining using light-emitting diodes 520 providing light 522 with sufficient intensity to photo-bleach fluorophores in fluorescent probes. Alternatively, chemicals 530 to detach fluorophores or fluorescent probes from target molecules in the cells can be supplied to the samples. Also, a laser 524 may be incorporated to provide bleaching light 526 to cells in the flow channel. The re-staining process 530 involves introducing another set of fluorescent probes 540 to the cells, targeting a different set of molecules different from the previous set of target molecules. These new set of probes may have the same set of fluorophores conjugated to different antibodies for different targets, or they may use different fluorophores. The stained samples are loaded into the same flow cell 314 enabling measurement with the new set of fluorescent probes.

FIG. 5B depicts a modified instrument for cyclic flow cytometry, in accordance with embodiments of the present invention. This instrument includes the system 552 depicted in FIG. 5, as well as a fluidics-based recirculatory apparatus 554 to automate the processes of cyclic flow cytometry including cell reconditioning. This instrument employs one or more reconditioning chambers 556-560 in series connected by tubing 568, in which cells are subjected to different treatments including chemical, thermal or light. The reconditioning chambers may also be temperature controlled and include sensors to probe the state of the reconditioning process. Each reconditioning chamber may be exposed to atmospheric pressure via valves 562-566. The pressure in each chamber may additionally be controlled via pressurized gas lines connected to the fluidics controller. In the latter case, pressure in each chamber is also monitored by the controller. The recirculator may also include one or more storage chambers 590 where cells reside while awaiting further processing. The multiple reconditioning chamber configuration utilizes numerous valves and pumps 570-578 to transport the sample between chambers. A number of pumps bay be used, including, but not limited to peristaltic pumps, displacement pumps, or pressure pumps. One or more sets of additional pumps and valves 580-586 allow the introduction of one or more types of external fluids to each chamber that can mix or interact with the cell sample. These ports also allow the introduction of cleaning agents to sanitize the chambers after the sample has been cleared out, or to extract the sample from the system. The various pumps and valves are electronically controlled by a fluidic controller 588. Additional pressured gas lines may be connected between the fluidics controller and each reconditioning chamber, in the case that pressure pumps are used for sample transport. At the end of each reconditioning cycle, the controller transports the sample to a storage chamber 590 before the flow cytometer 552 can begin a new measurement cycle.

Figure 6A:
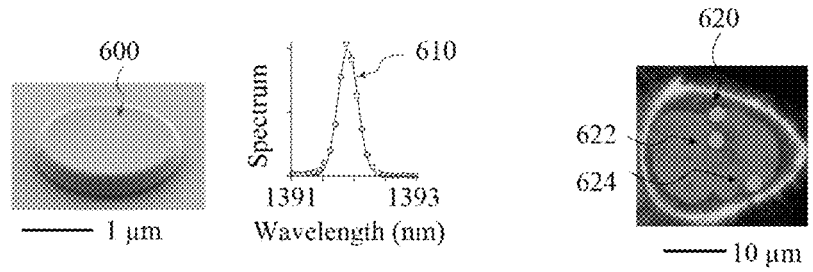
FIGS. 6A through 6D shows exemplary optical identifiers that can be used for tagging cells uniquely for use in embodiments of the present invention. Although these optical identifiers have become recently known in the art, their use in the present context is new.
Figure 6B:
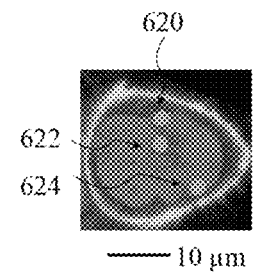
Figure 6C:
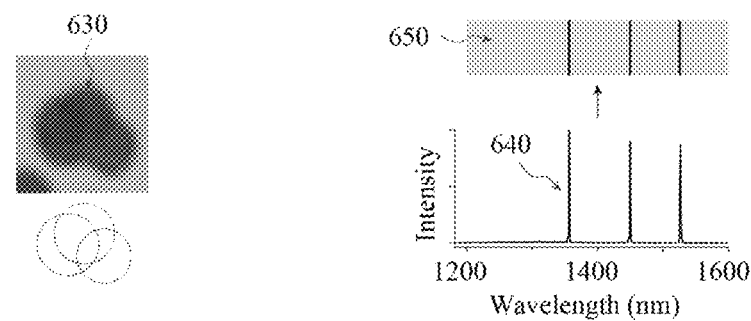
Figure 6D:
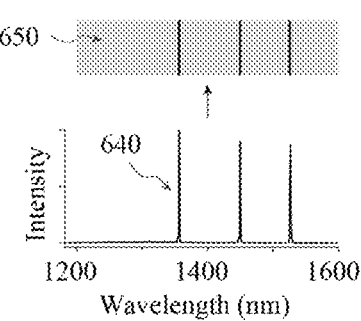

FIGS. 6A through 6D show exemplary optical identifiers that can be used for tagging cells uniquely for use in embodiments of the present invention. Although these optical identifiers have become recently known in the art, their use in the present context is new. FIG. 6A shows an electron microscope image of a silica-coated semiconductor micro-laser particle and its typical stimulated-emission spectrum with a peak at 1392 nm and a full-width-at-half-maxima of 0.35 nm. FIG. 6B shows a fluorescence microscope image of a cell comprising three micro-laser particles with different laser emission peaks. FIG. 6C shows an optical image of an optical identifier comprising three microdisk lasers. FIG. 6D illustrates the emission spectrum from the triplet laser particles. The three narrow spectral peaks define the unique OFID conferred by the optical identifier.

Recently a variety of schemes for tagging cells with optical identifiers have been demonstrated, including fluorescent polystyrene particles, upconverting nanoparticle micro-lasers, perovskite nanowires, and plasmonic nanoparticles. In particular, semiconductor microdisk lasers with a diameter of 0.5-3 μm are particularly appropriate for tagging a large number of cells (>1,000) uniquely without compromising cell viability. Upon optical excitation, these micro-laser particles emit narrowband laser light with a linewidth of less than 1 nm, with a center wavelength tunable over a large spectral range.

Cyclic cytometry requires optical identifiers that can be repeatedly measurable and stable over multiple cycles of the entire cytometry processes. For example, the optical identifiers should be stable after the photobleaching process of the fluorophores. The photobleaching process inactivate the vast majority of the fluorophores at the surface of inside cells. Typically, it is desirable that greater than 99% of the fluorophores are bleached or inactivated. Almost any types of fluorophores can be photobleached by prolonged, repeated photoexcitation. However, it is desirable to use fluorophores that can be bleached within a practical duration of time, for example 30 min, under practically attainable light intensity while the photobleaching process does not significantly affect cell viability due to photothermal and photochemical effects. In a simple model, the probability of being inactivated may be described as $P_B = 1 - e^{-t/\tau_B}$, where $\tau_B(I_B)$ represents the half-lifetime of the fluorophore under illumination with an intensity of $I_B$. For example, bleaching 99.9% of fluorophores in 30 min would require $T_B > 4.3$ min for a given $I_B$.

It is also essential to use optical identifiers with sufficient number of OFIDs to label cells in a sample substantially uniquely.

Let N denotes the total number of OFID's, and M the number of OFIDs used. The probability P of having unique OFIDs in a given set of M OFIDs is $P=(1-1/N)^{M-1}$, which is equal to $e^{-M/N}$ because N, M>>1. When M=N, P is 36.7%. Typically, N>>M, for example, when $M=10^6$, $N=10^7$ gives P=90.5%, $N=10^8$ gives P=99.0%.

In this calculation, M is also equal to the number of cells that are tagged. Depending on applications, M is equal to the entire number of cells in a sample or may represent a small fraction of the entire cell population in a sample. Typically, M ranges from 1,000 to 1,000,000.

In the case of micro-laser particles, N can range from $10^3$ to $10^{12}$ or more, depending on the number of micro-laser particles per cell. Assuming that each micro-laser particle can emit one of n=1000 distinguishable wavelengths, $N=C^R(n, r)=(n+r-1)!/r!(n-1)!$, where r is the number of micro-laser particles per cell. For n=1000, and r=1, N=1000. For n=1000, and r=3, $N=1.67\times10^8$. For n=1000, and r=5, $N=8.42\times10^{12}$.

Matching OFIDs involves using an algorithm to assign a series of measured OFIDs to a unique cellular entity with high probabilistic confidence (>95%). The algorithm contains a method to extract features from the measured OFIDs, including but not limited to spectral peak position, widths and how these properties change according to pump laser intensity. The algorithm also contains a method to calculate a distance metric or score between pairs of features, thereby allowing the assignment of a composite numerical score between two OFIDs based on all pairwise scores taken with one set of features from one OFID and a second set of features from another OFID. Finally, the algorithm also contains a method to determine the equivalence of two OFIDs, in the sense that they arise from the same physical set of optical identifiers, based on this composite numerical score.

In some cases, cells measured across different cycles may have missing, mismatched, or duplicate OFIDs. These errors are typically resolved by excluding these unmatched OFIDs and their respective cells from the analysis in silico. However, cells with unmatched OFIDs at one cycle may still be matched with cells from another cycle to a reasonable statistical degree of confidence by determining the most likely match based on the optical identifiers that are measured and/or the light scattering and fluorescence patterns of the cells.

To reduce the number of duplicate OFIDs to less than 10%, the number of possible OFIDs (M) should be 10 times greater than the number of cells in the sample (N). One strategy is to include redundancy in the OFID by labeling each cell with more optical identifiers than necessary.

FIG. 6 shows exemplary semiconductor laser particles that meet the requirement. A single micro-laser particle 600 can produce narrowband laser emission 610. Cells are allowed to uptake more than one micro-laser particle, 620, 622, and 624 with different emission wavelengths. Alternatively, the micro-laser particles may be combined together in the form of a multiplet 630 prior to delivery inside a cell. The combined laser emission 640 from the set of microdisks constitutes an OFID 650 of the cell. With three microdisks per cell on average, this scheme can produce N>10,000,000.

FIGS. 7A through 7D depict optical systems for collecting light from micro-laser particles, in accordance with embodiments of the present invention. For laser particles with substantially isotropic radiation patterns or omnidirectional, a single collection path is appropriate. However, laser particles have optical cavities, and the intensity of output laser emission is related to the coupling of the cavity to its surrounding environment. As a result, the emission pattern from a laser particle, such as the micro-laser particle, tends to be spatially nonuniform. This direction-dependent emission intensity can cause problems in the dynamic range and signal-to-noise ratio in the detection of the laser output spectrum. Collecting the emission 332 with as large numerical aperture or solid angle as possible can minimize the problems.

Figure 7A:
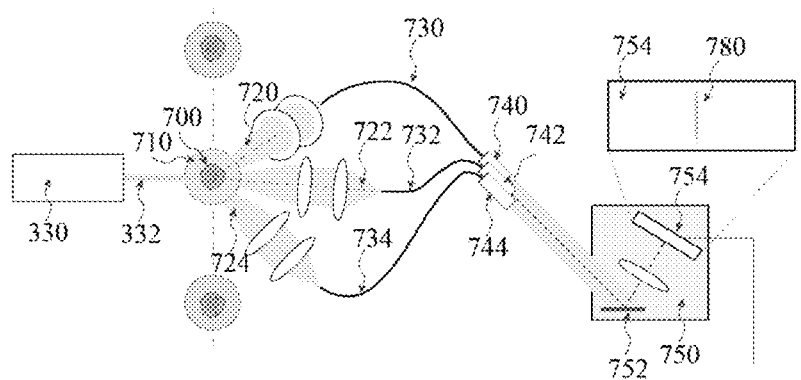
FIG. 7A through 7D depicts optical systems for collecting light from micro-laser particles, in accordance with embodiments of the present invention.

To further reduce the problem, instead of using a single path, the preferred embodiment may employ multiple collection paths. Two paths are likely to be adequate when the angle-dependence of laser particle emission is modest. Three paths could be more desirable if the direction dependence of laser emission is very strong. Four paths may also be used. FIG. 7A shows a system using multiple optical fibers to collect light from micro-laser particles. In this design, the emission from a cell 700 in an aqueous droplet 710 within three paths 720, 722, and 724 are detected. The three paths are approximately form 90-degree, 60-degree, or 120-degree with respect to each other. The emission beams 720, 722, and 724 are collected by optical fibers 730, 732, and 734.

At the distal ends of the fibers, lenses are placed to collimate the output beams and direct them to the grating 752 in the spectrometer 750. The collimators 740, 742, and 744 are arranged parallel to the grating pattern of the diffraction grating 342, so that the collected beams undergo same diffraction. The diffraction beams are focused onto the camera 754. For example, when the laser particle emits a single laser line, the three beams form an elongated pattern 780 in the camera. The entire pattern can fall onto a single pixel in when the CCD has a line array with a high aspect ratio of pixel size (e.g. 500 µm×10 µm), or onto different pixels along the vertical dimension that is orthogonal to the diffraction plane if a two-dimensional CCD array is used. In the latter case, the pixel data are integrated along the vertical dimension to produce the output spectrum. Various different optical schemes for multiple-path beam collection known to the skilled in the art may be used, including free-space setups with beam combiners.

Figure 7B:
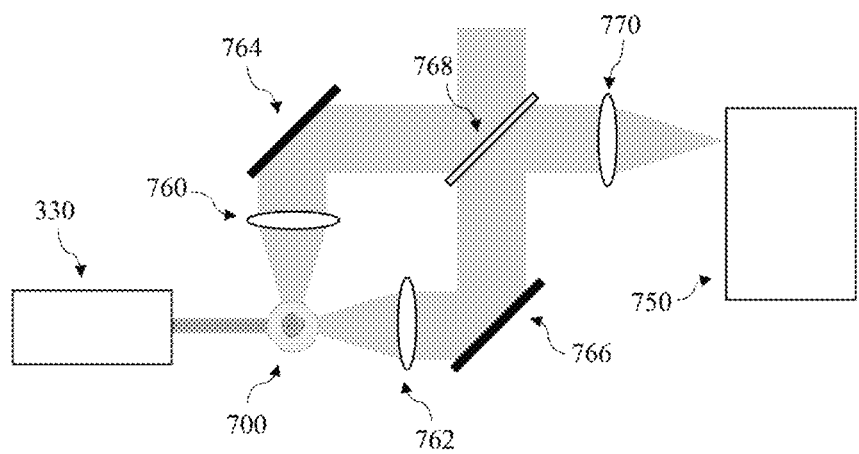

FIG. 7B depicts an alternative optical configuration using two collection paths and free-space optics only. A pump laser 330 excites the optical identifiers contained within a cell 700 which is flowing into the plane of the page. Light collected by the two collection paths are roughly collimated by lenses 760 and 762, placed at 90 degrees to each other. The light is then redirected by mirrors 764 and 766 before being combined by a beamsplitter 768 The combined light is subsequently focused into a spectrometer 750 by lens 770.

Figure 7C:
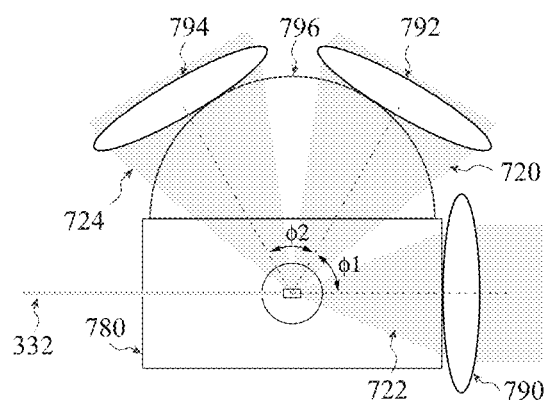
Figure 7D:
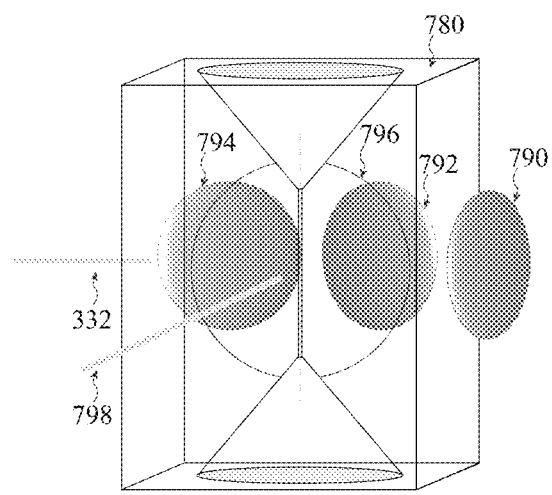

FIG. 7C depicts yet another optical configuration using three collection paths. A flow cell 780 provides a flow channel. A pump laser light 332 excites the optical identifier contained within a cell that is in the continuous flow along the channel. Light emitted from the micro-laser particles approximately in the forward direction 722 is collected by a lens 790 and collimated or focused for measurement. Light emitted with angles φ1 and φ2 with respect to the pump direction are collected a lens 792 and lens 794, respectively. Approximately, φ1 and φ2 are 60 degrees for minimizing the angular dependence of emission from the micro-laser particles. To reduce optical aberration of the emission beams at the interface of the flow cell and the air, a solid immersion lens, such as a hemisphere glass 796, may be used. The collimated light after the lenses 790, 792, and 794 may be launched into optical fibers and directed to a spectrometer. FIG. 7D depicts a 3-dimensional drawing of the configuration in FIG. 7C.

When a cell contains multiple micro-laser particles, the pump light 332 is partially absorbed and partially reflected by each laser particle. When the laser particles are positioned such that one particle is behind another particle along the path of the pump light, the next particle may receive less pump energy than the particle in the front. This results in different magnitude of emission from the two laser particles. In the event when the attenuation of the pump light by each laser particle is significant, the next particle may not receive sufficient pump energy for lasing. To minimize this problem, additional pump light 798 may be arranged so that cells are illuminated with two pump beams in approximately two orthogonal directions. This can reduce the pump shadowing effect. More than two pump beams may be used to minimize the difference of pump energy received by different laser particles.

Figure 8:
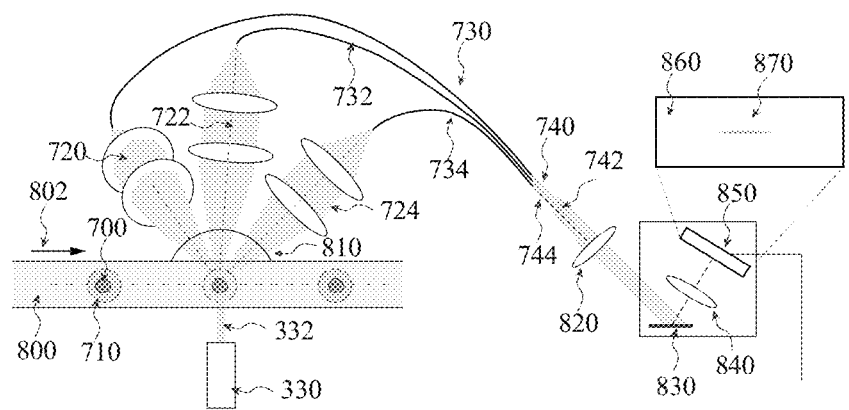
FIG. 8 depicts an optical system for collecting light from micro-laser particle in a microfluidic device, in accordance with embodiments of the present invention.

FIG. 8 depicts an optical system for collecting light from micro-laser particle in a microfluidic device, in accordance with embodiments of the present invention. This system employs a microfluidic chip 800 providing a flow 802. Three collection optics are depicted, which are the same as in FIG. 7. To avoid beam aberration from the mismatch of the refractive index between the microfluidic chip material and the surrounding air, a glass or plastic semi-spherical lens 810 may be used.

In this configuration, the distal ends of the fibers 730, 732, and 734 are stacked to a linear array. The beams 740, 742, and 744 exiting the fibers are collimated by a single lens 820 and diffracted by a diffraction grating 830, which has grating lines parallel to the orientation of the stack of fibers. The diffraction beams are focused by a compound lens 840 onto a camera 860, in which a CCD array is arranged approximately orthogonal to the orientation of the fiber array and grating lines to receive the diffraction pattern 870. The fibers may be multimode fibers with a core size of 50 to 105 µm and a cladding size of 125 µm, with numerical aperture of approximately 0.22.

Figure 9A:
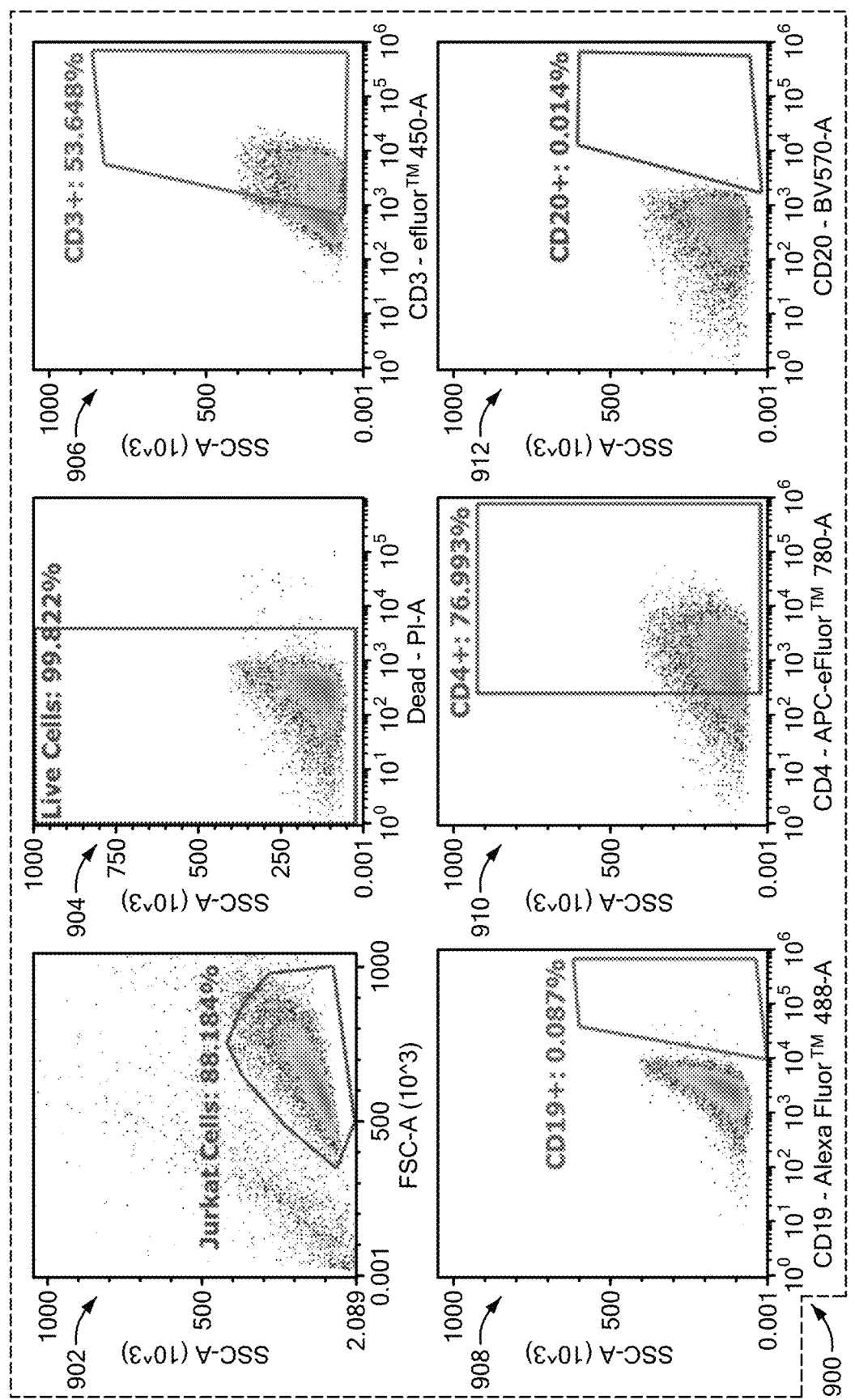
FIG. 9A through 9B shows a comparison of flow cytometry data of cells obtained with and without micro-laser particles.
Figure 9A:
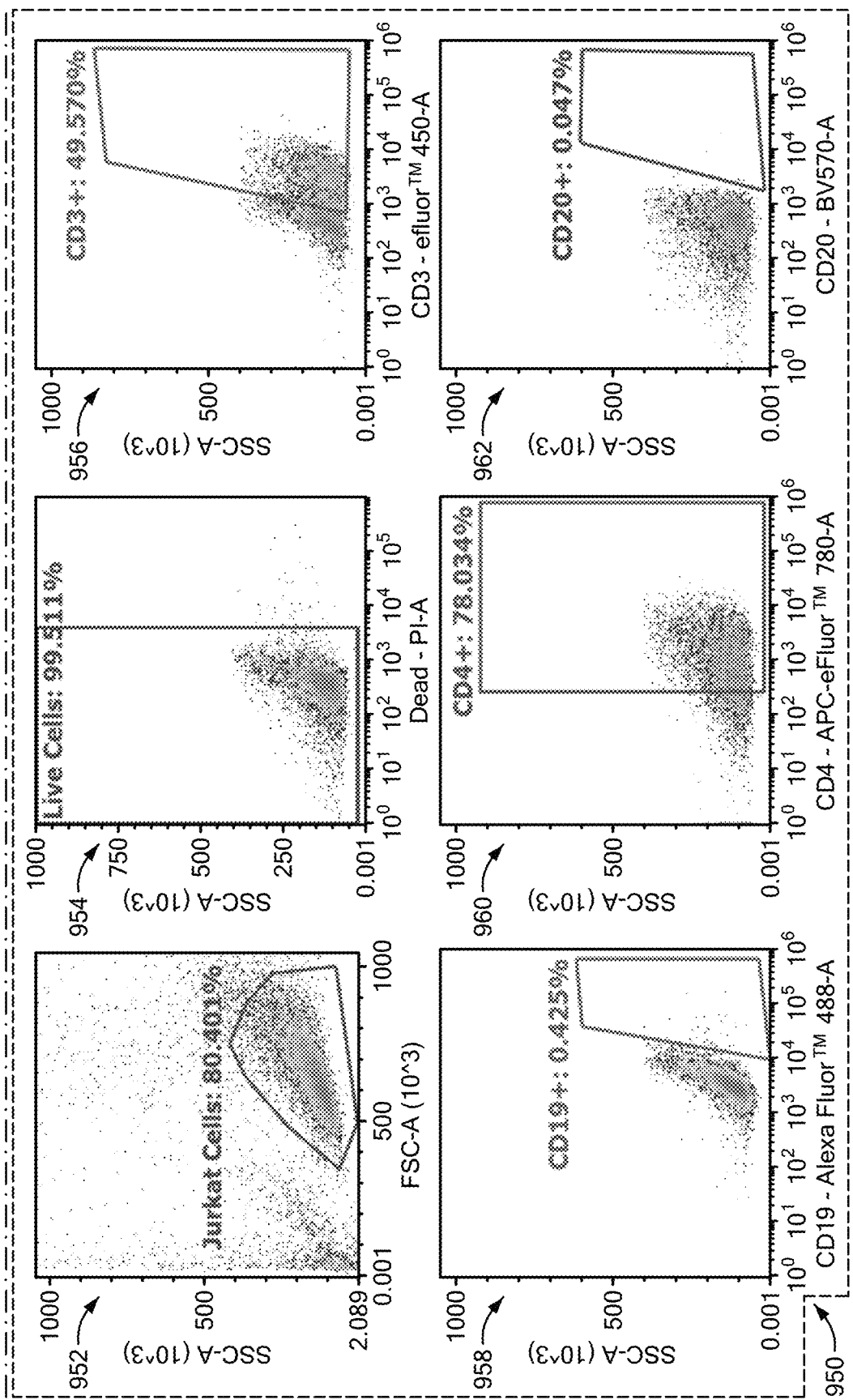
Figure 9B:
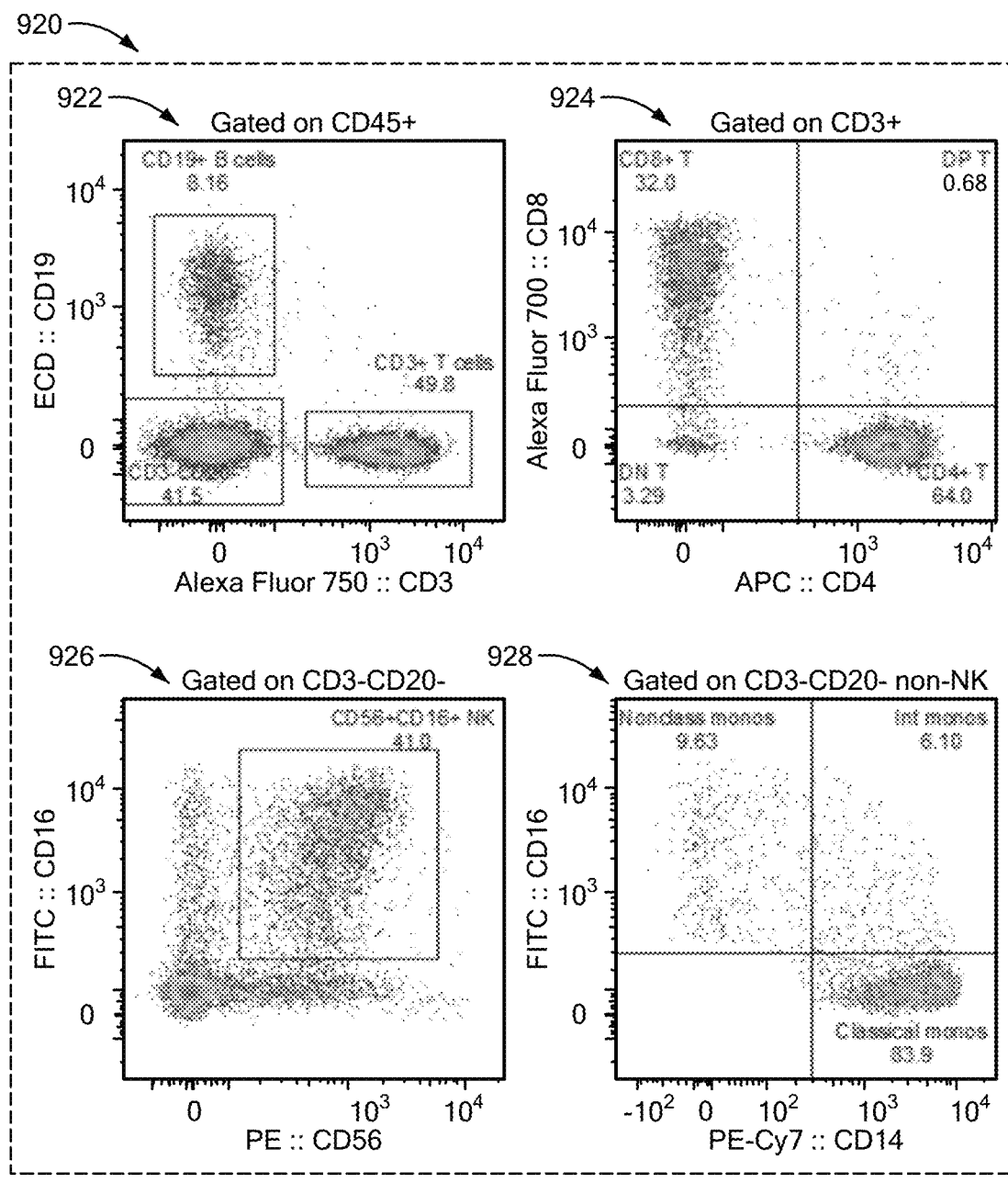
Figure 9B:
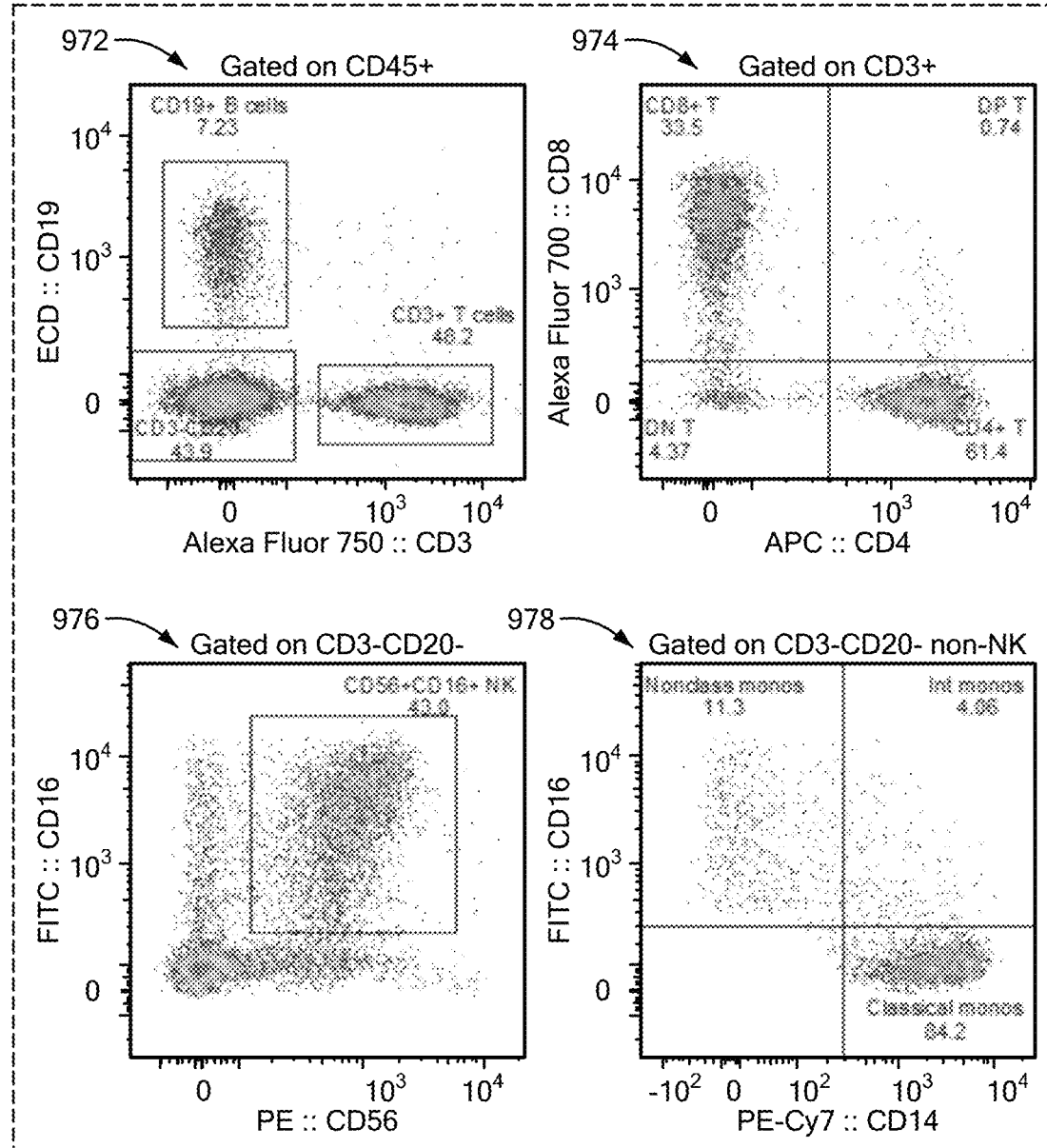

FIGS. 9A and 9B show a comparison of flow cytometry data of cells obtained with and without micro-laser particles. FIG. 9A shows data of Human Jurkat T cells without micro-laser particles 900 and tagged with micro-laser particles 950. The data shows that the presence of micro-laser particles does not cause significant changes in the scattering profiles 902 and 952, cell viability 904 and 954, CD3 staining 906 and 956, CD19 staining 908 and 958, CD4 staining 910 and 960, and CD20 staining 912 and 962. FIG. 9B shows data of human primary peripheral blood mononuclear cells (PBMCs) without micro-laser particles 920 and tagged with micro-laser particles 970. The data shows that the presence of micro-laser particles does not cause significant changes in CD3 versus CD19 staining 922 and 972, CD8 versus CD4 staining 924 and 974, CD16 versus CD56 staining 926 and 976, and CD16 versus CD14 staining 928 and 978.

Figure 10A:
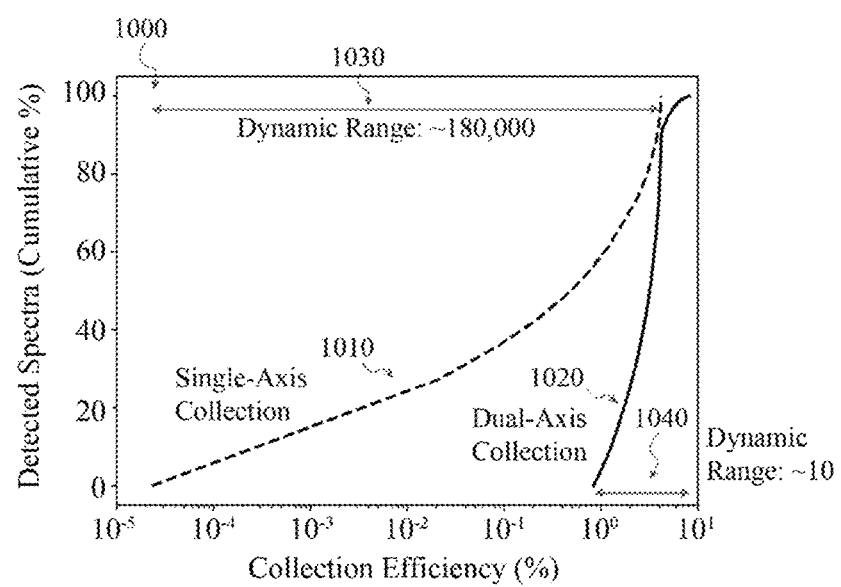
FIGS. 10A through 10B shows simulated and experimental data, respectively, from a modified flow cytometer prototype to read cells labeled with optical identifiers, in accordance with embodiments of the present invention.
Figure 10B:
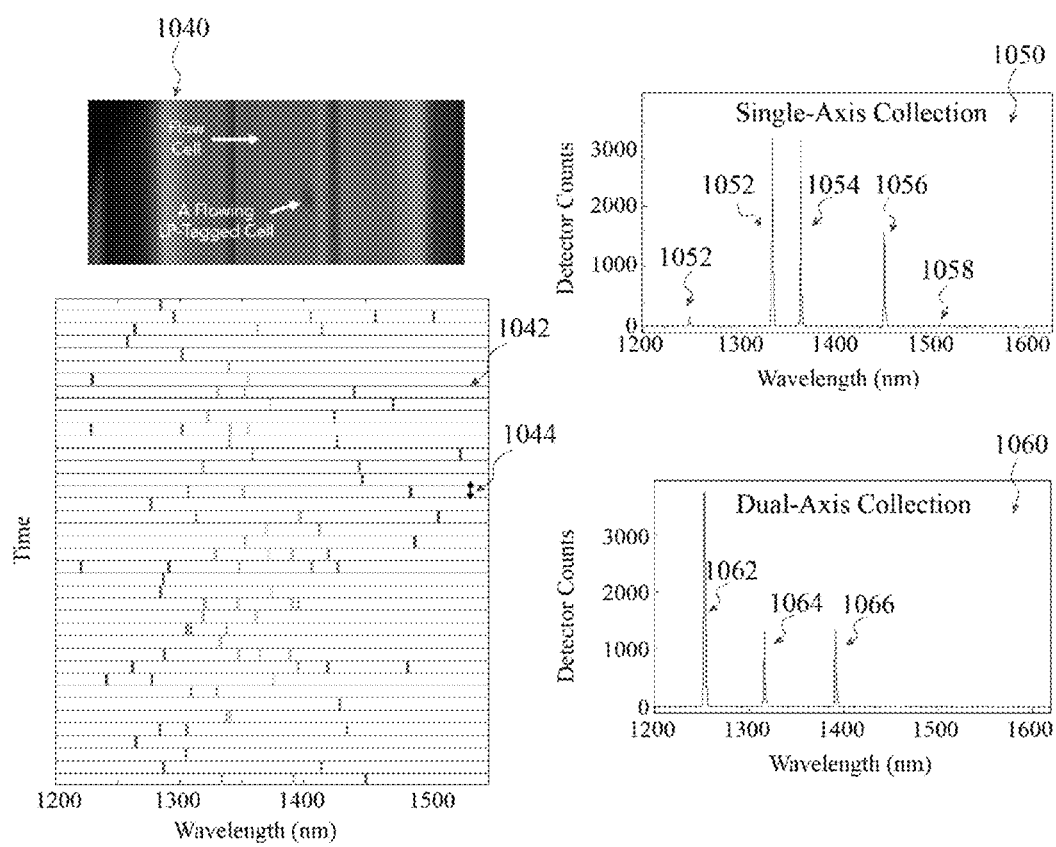

FIGS. 10A through 10B show simulated and experimental data from a modified flow cytometer prototype to read cells labeled with optical identifiers, in accordance with embodiments of the present invention. FIG. 10A shows the cumulative percentage of detected spectra for a given collection efficiency in a simulation of randomly oriented microdisk laser particles 1000. The dashed line 1010 shows the result for a system with a single optical collection path, while the solid line 1020 shows the result for a system with dual optical collection paths. In this simulation, when a microdisk is oriented optimally to the collection lens (assumed to have numerical aperture of 0.4), the total percentage of light collected is 4% for a single-axis configuration and 8% for a dual-axis configuration. The minimum required dynamic range to detect all the spectral peaks is depicted within the blue arrows: for single-axis 1030, the required dynamic range is 180,000, for dual-axis 1040, the required dynamic range is ~10. The required dynamic range for the single-axis simulation far exceeds the capabilities of a typical CCD, PMTs, and photodetectors when factoring in readout noise, sensitivity and dynamic range (typically <10,000). In comparison, the significantly reduced signal variation in the dual-axis detection can be easily accommodated with a spectrometer employing a CCD camera and analog-to-digital converters (ADCs).

FIG. 10B shows exemplary data obtained using a modified flow cytometer prototype, in accordance with embodiments of the present invention. An OFID reader, consisting of a 1064-nm pump laser with a 10 MHz repetition rate and a spectrometer was employed in conjunction with a capillary-based flow cytometer. The system was tested with single and dual-axis collection paths. A white-light image 1040 of a flowing micro-laser particle tagged cell in a flow cell is shown. As cells flow through the flow cell, OFID spectra are acquired and recorded in a computer 1042. Each of the rows delimited by the black lines correspond to the OFID (depicted in lines with different colors for different laser emission peaks) of a particular cell 1044. We tested the system with single and dual-axis collection paths. A representative OFID spectra collected with the single-axis configuration 1050 shows micro-laser particle emission peaks 1052-1058 that vary several orders of magnitude in intensity. In comparison, a representative OFID spectra collected with the dual-axis configuration 1060 shows micro-laser particle emission peaks 1062-1066 that vary less than one order of magnitude in intensity.

Figure 11A:
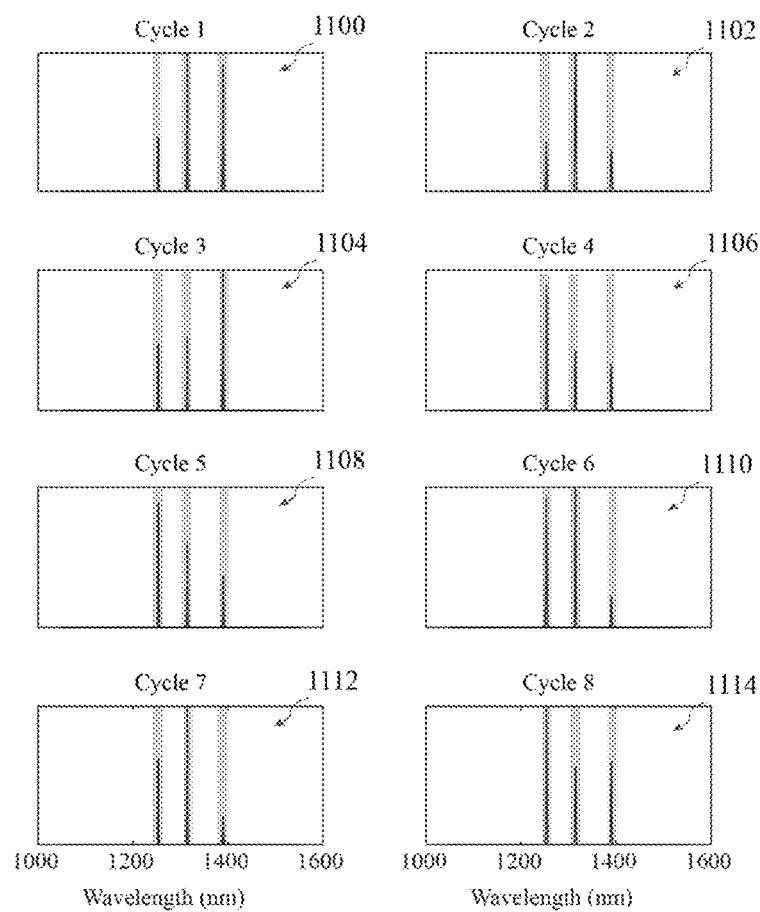
FIGS. 11A through 11B shows exemplary data obtained using a cyclic flow cytometry prototype instrument for measuring cells labeled with optical identifiers over multiple cycles, in accordance with embodiments of the present invention.
Figure 11B:
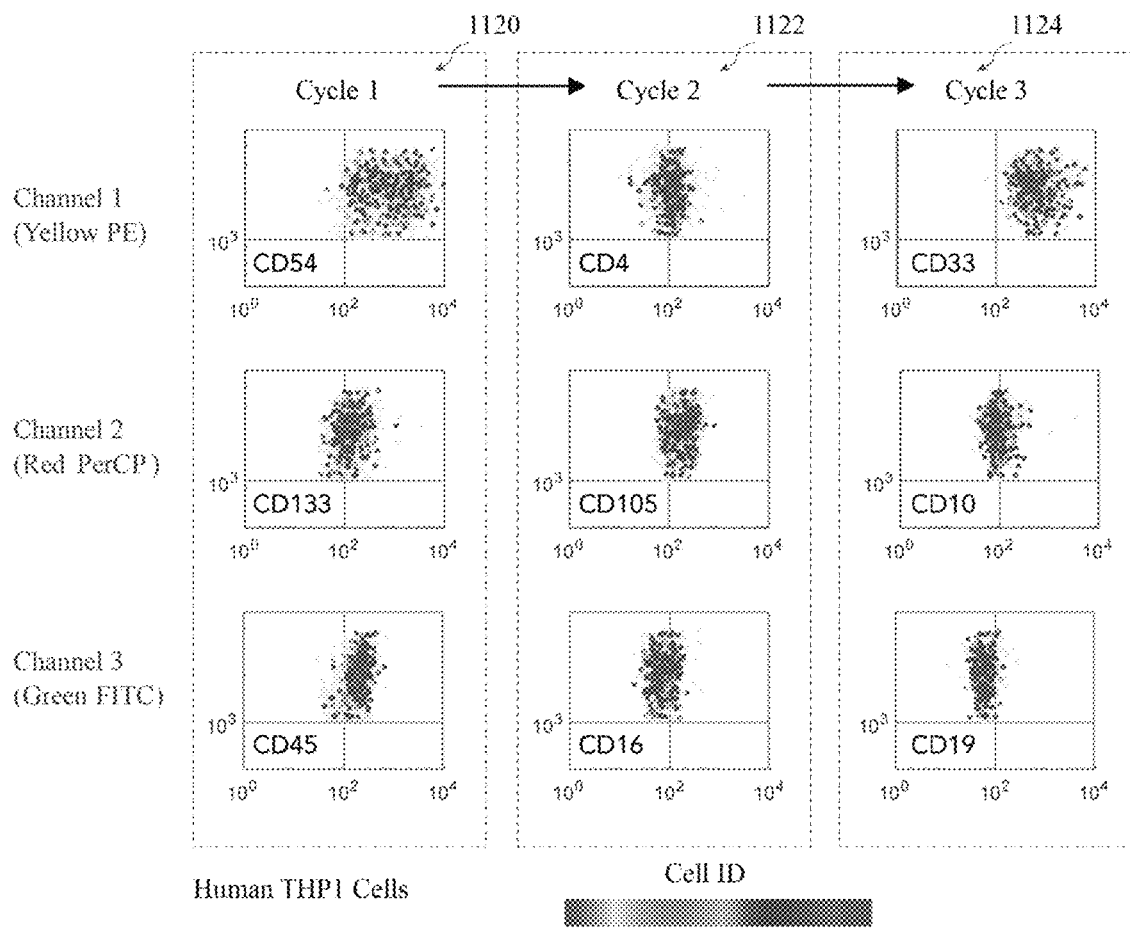

FIGS. 11A through 11B shows exemplary data obtained using a cyclic flow cytometry prototype instrument for measuring cells labeled with optical identifiers over multiple cycles, in accordance with embodiments of the present invention. A dual-axis collection configuration was used to read the micro-laser particle emission. The prototype has a total of 5 PMTs to measure forward scattering, side scattering, and 3 fluorescence spectra. The pump laser light of the OFID reader was coupled such that both fluorescence excitation light and pump light illuminate cells in a flow channel through a common objective lens. A dichroic beam splitter was employed to separate the NIR emission of laser particles from fluorescence emission of fluorescent probes.

FIG. 11A shows an exemplary cell associated with micro-laser particle generating an OFID consisting of three spectral peaks that is measured and identified over 8 successive flow cycles of measurement 1100-1114. Small variations in the intensity of each peak does not affect the ability of the algorithm to match OFIDs between cycles.

FIG. 11B shows proof-of-concept flow cytometry data in which THP1 cells tagged with micro-laser particles were analyzed over three flow cycles 1120-1124. Staining and re-conditioning was performed to target 3 different markers per cycle. After the first flow measurement, cells were collected. The existing fluorescent antibodies in the cells were removed (using chemically released antibodies), and a new set of three fluorescent antibodies were used to stain the cells. The stained cells were loaded into the instrument for a second flow measurement. After the measurement, a third set of fluorescent antibodies were applied to the cells that were collected. And, a third flow measurement was performed. A personal computer was used to store fluorescence data from the PMT's and spectrometer data of each cells. A custom-written software was used to associate the fluorescence data with the OFID of each cell in each of the three measurements and to use the OFID to combine attributes of the corresponding target sets of parameters. Matching of OFIDs between cycles enabled a total of 9 different markers to be measured per cell.

Figure 12:
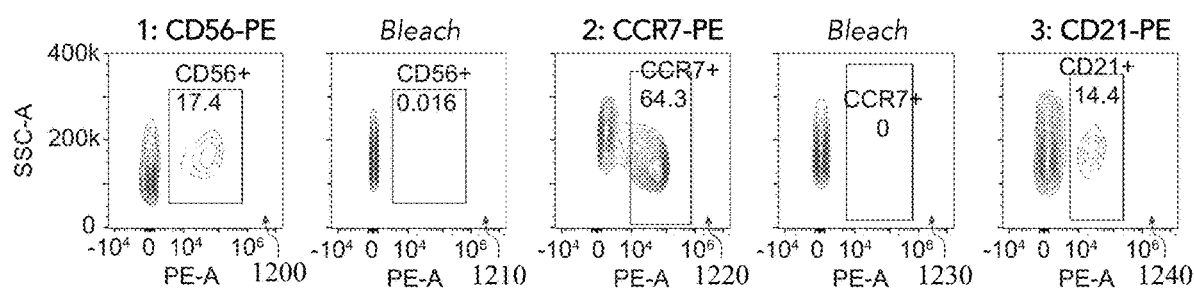
FIG. 12 shows exemplary data showing reconditioning of human PBMCs for multiple cycles of measurement through photobleaching, in accordance with embodiments of the present invention.

FIG. 12 shows proof-of-concept data showing reconditioning of human PBMCs for multiple cycles of measurement. A high-power white light-emitting diode (LED) with an output power of >3 W was used to photobleach fluorophore-conjugated antibodies attached to cells between measurements. Typically, 30 minutes of white light illumination was required for complete photobleaching of stained cells which was also performed at 4 degrees to maintain cell viability. Cells were first stained with CD56-phycoerythrin (PE) and measured on a flow cytometer 1200. Next, the cells were bleached to completely inactivate the fluorescent signals 1210 from the PE antibodies. The cells were then stained for CCR7-PE and measured again on a flow cytometer 1220. Next, the cells were bleached to completely inactivate the fluorescent signals 1230 from the PE antibodies. Finally, the cells were stained for CD21-PE and measured again on a flow cytometer 1240. The data showed no significant difference in the proportions of different cell types in cell samples that were photobleached compared to control samples with no photobleaching.

Figure 13:
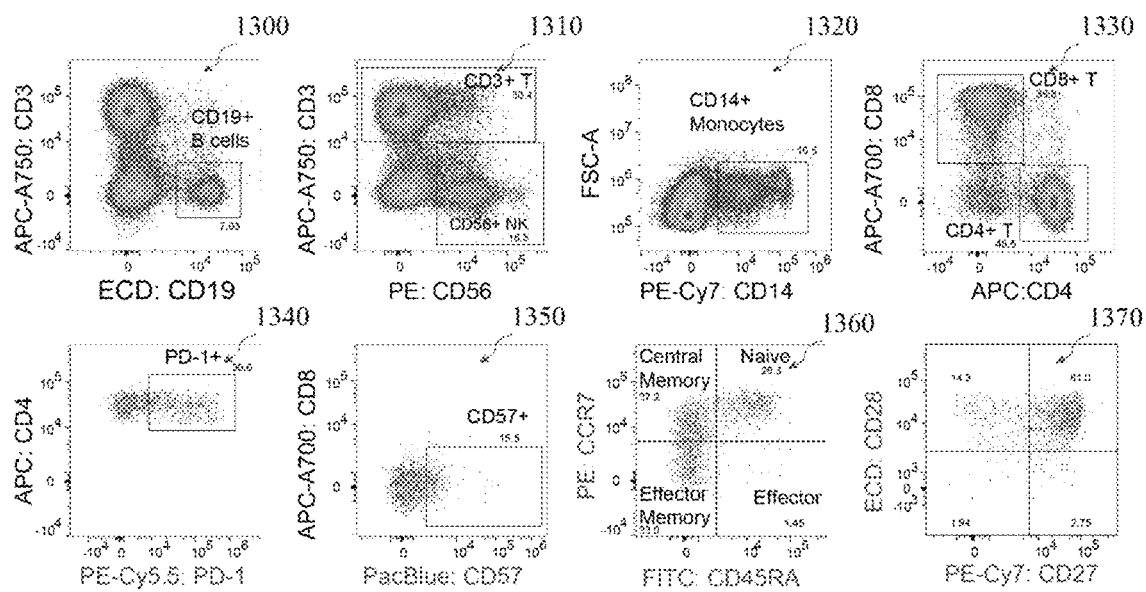
FIG. 13 shows exemplary data obtained using a cyclic flow cytometry prototype instrument to characterize different immune cell populations of human PBMCs, in accordance with embodiments of the present invention.

FIG. 13 shows proof-of-concept flow cytometry data in which human PBMCs tagged with micro-laser particles were analyzed over two flow cycles to measure the proportions of different immune cell populations. Freshly thawed PBMCs were tagged with micro-laser particles such that most of the cells contained 3 or more micro-laser particles to generate a unique OFID. About 500,000 cells in a volume of 100 μL were measured at a speed of 30 μL/min. In the first pass, the tagged cells were stained with fluorophore-conjugated antibodies including CD3-APCA750, CD19-ECD, CD56-PE, CD14-PE-Cy7, CD8-APCA700, and CD4-APC, and measured using a cyclic flow cytometry prototype instrument equipped with an OFID reader. The fluorophores were chosen in part because of their ability to be photobleached with minimal loss in cell viability. After photobleaching the tagged cells with a white LED for 30 minutes (similar to what was described in FIG. 12), the cells were washed and re-stained with a second set of fluorophore-conjugated antibodies including PD1-PECy5.5, CD57-PacBlue, CD45RA-FITC, CCR7-PE, CD28-ECD, and CD27-PECy7, and measured on the cyclic flow cytometer. The fluorescence data was matched using the OFID of each cell between cycles to generate a dataset with 12 different markers per cell. This data was used to characterize the frequencies of different lymphocytes 1300, natural killer cells 1310, monocytes 1320, T cells 1330, and subsets of CD4+ T cells 1340, 1340, 1360 and 1370.

This invention describes a system and method to perform cyclic flow cytometry. This invention overcomes current challenges in cost, difficulty, and accuracy of highly multiplexed flow cytometry. This invention can eliminate the need of the elaborate and costly spectral unmixing processes or significantly reduce the burden of selecting, optimizing and testing a panel. This invention can allow for highly multiplexed cytometry with lower cost and higher accuracy. The instrument costs are substantially lower than state-of-the-art flow cytometers as complex fluorescence detection schemes involving many lasers and detectors are not necessary to measure 30 markers at once. Reagent costs are also reduced as not as many antibodies are needed in the workflow to prepare the flow cytometry panel, particularly for fluorescence minus one (FMO) controls, as described previously.

Furthermore, with multiple flow cycles, the number of analyzed molecular contents from each cell can be made much greater (e.g. >30 targets) than possible with single-pass or single-run, state-of-the-art flow cytometers. For example, by measuring 10 markers in each run, 4 runs would allow 40 markers overall to be measured.

The preferred embodiments described herein are to analyze cells. However, instead of whole cells, the apparatus and method can also be used for analyzing a part of cells, such as the cellular nuclei, other organelles, or cellular extracts such as exosomes. For example, the nuclei of a set of cells are extracted and tagged with optical identifiers. The embodiment shown in FIG. 5 receives the nuclei, instead of cells 300, as a sample, and process the sample in the same way as described.

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A method of performing cyclic flow cytometry analysis on a sample population of cellular entities, the method comprising:
   causing each cellular entity in the population to be labeled with an optical identifier; and
   for each cellular entity in the population:
   (i) performing a first pass of flow cytometry measurement over a flow channel with respect to a first set of parameters,
   (ii) determining an identification for the cellular entity, for which values of the first set of parameters are being obtained,
   (iii) storing the values of the first set in association with the identification,
   (iv) performing a second pass of flow cytometry measurement over the flow channel with respect to a second set of parameters,
   (v) determining, separately, the identification for the cellular entity, for which values of the second set of parameters are being obtained, and
   (vi) storing the values of the second set in association with the identification.

2. A method according to claim 1, further comprising, for each cellular entity in the population, using the identification to combine attributes of the first set of parameters with attributes of the second set of parameters.

3. A method according to claim 1, further comprising:
   performing at least one additional pass of flow cytometry measurement over the flow channel with respect to an at least one additional set of parameters,
   determining, separately, the identification for the cellular entity for which values of the at least one additional set of parameters are being obtained, and
   storing the values of the at least one additional set in association with the identification.

4. A method according to claim 1, wherein the first and second passes of flow cytometry measurement use first and second sets of fluorescent probes respectively targeting distinct sets of parameters, and the method further comprises after performing the first pass of flow cytometry measurement and before performing the second pass of flow cytometry measurement, inactivating the first set of fluorescent probes.

5. A method according to claim 1, wherein the sample population includes at least 1,000 cellular entities.

6. A method according to claim 1, further comprising, after performing the first pass of flow cytometry measurement and before performing the second pass of flow cytometry measurement, collecting the population that has been made the subject of the analysis in a manner preserving characteristics of the cellular entities in the population.

7. A method according to claim 6, wherein collecting includes using a collection vessel at an end of the flow channel to capture the cellular entities of the population.

8. A method according to claim 7, further comprising reconditioning the captured cellular entities before performing the second pass of flow cytometry measurement.

9. A method according to claim 1, wherein the optical identifier is a set of micro-laser particles.

10. A method according to claim 9, wherein the micro-laser particles include a semiconductor.

11. A method according to claim 1, wherein the flow cytometry measurements utilize fluorescence by fluorophores, and determining the identification for the cellular entity includes reading the optical identifier in an emission frequency spectrum using a light excitation source.

12. A method according to claim 11, wherein the fluorophores are configured to be photobleachable within 30 min without affecting cell viability.

13. A method according to claim 11, wherein the fluorophores are configured to operate in a fluorescence frequency spectrum separate from the emission frequency spectrum.

14. A method according to claim 1, wherein the first set of parameters is selected from the group consisting of surface or intracellular protein expression, RNA expression, quantification of organelles (such as mitochondria and lysosomes), cell granularity, cell size, cell shape and combinations thereof.

15. A method according to claim 14, wherein each such parameter of the cellular entity is measured by a phenomenon selected from the group consisting of fluorescence, light scattering, and absorption.

16. An improved flow cytometry apparatus having a flow channel coupled to a flow input configured to receive a sample population of cellular entities to be measured, with respect to a target set of parameters, wherein the improvement comprises:
   an OFID reader associated with the flow channel, wherein each cellular entity in the sample population has been tagged with an optical identifier, and the OFID reader is configured to determine an identification of each cellular entity as it is being measured in each pass of a plurality of passes of the sample population of cellular entities through the flow channel, each pass associated with a corresponding target set of parameters.

17. An improved flow cytometry apparatus according to claim 16, in which the OFID reader is configured to operate over a plurality of emission collection paths, of which two thereof define an angle of approximately 90 degrees with respect to each other.

18. An improved flow cytometry apparatus according to claim 16, further comprising a recirculator configured to recondition cellular entities that have passed through the flow channel and to position them for a further pass through the flow channel.

19. An improved flow cytometry apparatus having a flow channel coupled to a flow input configured to receive a sample population of cellular entities to be measured, with respect to a target set of parameters, wherein the improvement comprises:

an OFID reader associated with the flow channel, wherein each cellular entity in the sample population has been tagged with an optical identifier, and the OFID reader is configured to determine an identification of each cellular entity as it is being measured in each pass of a plurality of passes of the sample population of cellular entities through the flow channel, each pass associated with a corresponding target set of parameters; and a processor (i) to associate and store in a storage device a corresponding fluorescence reading with the identification of each cellular entity in each of the passes and (ii) to use the identification to combine attributes of the corresponding target sets of parameters.

20. An improved flow cytometry apparatus according to claim 19, wherein the OFID reader is configured to operate over a plurality of emission collection paths of which two thereof define an angle of approximately 90 degrees with respect to each other.

21. An improved flow cytometry apparatus according to claim 19, wherein the improvement further comprises a recirculator configured to capture and recondition cellular entities that have passed through the flow channel and to position them for a further pass through the flow channel.

22. An improved flow cytometry apparatus according to claim 21, wherein the recirculator has a surface, for contacting the population of cellular entities that is configured to have low wettability.

23. An improved flow cytometry apparatus having a flow channel coupled to a flow input configured to receive a sample population of cellular entities to be measured, with respect to a target set of parameters, wherein the improvement comprises:

an OFID reader associated with the flow channel, wherein each cellular entity in the sample population has been tagged with an optical identifier, and the OFID reader is configured to determine an identification of each cellular entity as it is being measured in the flow channel, wherein the OFID reader is configured to operate over a plurality of emission collection paths of which two therefore define an angle of approximately 90 degrees with respect to each other; and a processor (i) to associate and store in a storage device a corresponding fluorescence reading with the identification of each cellular entity and (ii) to use the identification to combine attributes of the target set of parameters.

24. A kit for converting a flow cytometry apparatus having a flow channel coupled to a flow input configured to receive a sample population of cellular entities to be measured, with respect to a target set of parameters, into an improved flow cytometry apparatus, the kit comprising:

an OFID reader associated with the flow channel, wherein each cellular entity in the sample population has been tagged with an optical identifier, and the OFID reader is configured to determine an identification of each cellular entity as it is being measured in each pass of a plurality of passes of the sample population of cellular entities through the flow channel, each pass associated with a corresponding target set of parameters;

a recirculator configured to capture and recondition cellular entities that have passed through the flow channel and to position them for a further pass through the flow channel; and a processor (i) to associate and store in a storage device a corresponding fluorescence reading with the identification of each cellular entity in each of the passes and (ii) to use the identification to combine attributes of the corresponding target sets of parameters.

* * * * *